US008239171B2

(12) United States Patent
Gamache et al.

(10) Patent No.: US 8,239,171 B2
(45) Date of Patent: Aug. 7, 2012

(54) SYSTEM AND METHOD OF ELIMINATING INTERFERENCE FOR IMPURITIES MEASUREMENT IN NOBLE GASES

(75) Inventors: Yves Gamache, Adstock (CA); André Fortier, Adstock (CA)

(73) Assignee: Panalytique Inc., Quebec (CA)

( * ) Notice: Subject to any disclaimer, the term of this patent is extended or adjusted under 35 U.S.C. 154(b) by 363 days.

(21) Appl. No.: 12/280,712

(22) PCT Filed: Feb. 28, 2007

(86) PCT No.: PCT/CA2007/000314
§ 371 (c)(1),
(2), (4) Date: Aug. 26, 2008

(87) PCT Pub. No.: WO2007/098586
PCT Pub. Date: Sep. 7, 2007

(65) Prior Publication Data
US 2009/0132206 A1 May 21, 2009

Related U.S. Application Data

(60) Provisional application No. 60/776,921, filed on Feb. 28, 2006.

(51) Int. Cl.
*H03F 1/26* (2006.01)
(52) U.S. Cl. .......... 702/190; 702/32; 702/189; 702/191; 356/316
(58) Field of Classification Search ............. 702/32, 702/189–190
See application file for complete search history.

(56) References Cited

U.S. PATENT DOCUMENTS

| 3,032,654 | A | | 5/1962 | Fay et al. |
| 3,141,739 | A | * | 7/1964 | Lewis et al. ............. 423/262 |
| 3,524,305 | A | | 8/1970 | Ives |
| 3,714,421 | A | | 1/1973 | Josias et al. |
| 3,967,113 | A | * | 6/1976 | Soodak et al. ............ 250/214 C |
| 4,148,612 | A | | 4/1979 | Taylor et al. |
| 4,713,224 | A | | 12/1987 | Tamhankar et al. |

(Continued)

FOREIGN PATENT DOCUMENTS
EP  0 246 572 A2  11/1987
(Continued)

OTHER PUBLICATIONS

Ogino, H. and Seki, T., Development of a Detector for Ultratrace Nitorgen in Argon Using Low-Pressure, Capillary Glow Discharge Molecular Emission Spectrophotometry, Sep. 1, 1997, Analytical Chemistry, vol. 69 No. 17, pp. 3636-3640.*

(Continued)

*Primary Examiner* — Jonathan C Teixeira Moffat
*Assistant Examiner* — Mischita Henson
(74) *Attorney, Agent, or Firm* — Daly, Crowley, Mofford & Durkee, LLP

(57) ABSTRACT

The invention provides a system and a method of eliminating interference for impurities measurement in noble gases based on emission spectroscopy which provide very stable, sensitive and interference free results. The method mainly relies on the use of a combination of particularly designed means serially connected for cancelling interferences and proper means for correcting linearity issues. The proposed method is particularly advantageous since it offers long-term stability while providing very accurate and reliable results, even at sub-ppb and up to 10,000 ppm levels, whatever the surrounding conditions and the additional impurities that could be present in the gas under analysis.

33 Claims, 18 Drawing Sheets

FUNCTIONAL BLOCK DIAGRAM OF THE PROPOSED PLASMA EMISSION BASE SYSTEM, WITH REFERENCE CELL

U.S. PATENT DOCUMENTS

| | | | |
|---|---|---|---|
| 4,801,209 A | | 1/1989 | Wadlow |
| 4,851,683 A | | 7/1989 | Yang et al. |
| 4,898,465 A | | 2/1990 | Crawford et al. |
| 5,009,099 A | | 4/1991 | Wells et al. |
| 5,135,549 A | | 8/1992 | Phillips et al. |
| 5,152,176 A | | 10/1992 | Bryselbout et al. |
| 5,168,323 A | | 12/1992 | Purtschert et al. |
| 5,325,705 A | * | 7/1994 | Tom .............................. 73/31.03 |
| 5,412,467 A | | 5/1995 | Malczewski et al. |
| 5,570,179 A | | 10/1996 | Weckstrom |
| 5,612,489 A | | 3/1997 | Ragsdale et al. |
| 5,831,728 A | | 11/1998 | Malczewski et al. |
| 6,040,915 A | * | 3/2000 | Wu et al. ....................... 356/435 |
| 6,043,881 A | | 3/2000 | Wegrzyn et al. |
| 6,341,520 B1 | | 1/2002 | Satoh et al. |
| 6,679,093 B2 | | 1/2004 | Johnson et al. |
| 7,216,528 B2 | | 5/2007 | Gamache et al. |
| 7,451,634 B2 | | 11/2008 | Gamache et al. |
| 2004/0036038 A1 | * | 2/2004 | Okumura et al. .......... 250/492.2 |
| 2006/0122448 A1 | * | 6/2006 | Thiagarajan et al. ......... 585/659 |
| 2009/0165642 A1 | | 7/2009 | Gamache et al. |
| 2010/0263529 A1 | * | 10/2010 | Alban et al. ....................... 95/41 |

FOREIGN PATENT DOCUMENTS

| | | | |
|---|---|---|---|
| JP | 2004047696 | * | 2/2004 |
| WO | WO 2006/089412 A | | 8/2006 |
| WO | WO 2007/045068 | | 4/2007 |
| WO | WO 2007/098586 | | 9/2007 |

OTHER PUBLICATIONS

Notification of Transmittal of the International Search Report and the Written Opinion of the International Searching Authority, or the Declaration and the International Preliminary Report on Patentability; PCT/CA2007/000314 dated Jun. 8, 2007, 12 pages.

Smid et al.: "Optical Emission Spectroscopy in HMDSO/O$_2$ RF Glow Discharge", WDS'05 Proceedings of Contributed Papers, Part II, pp. 408-413, 2005. ISBN 80-86732-59-2.

Verzele, et al., "Determination of traces of nitrogen and argon in oxygen by a simple gas chromatographic method", J. of Chromatography, vol. 209, 1981, pp. 455-457, XP002505132.

PCT International Preliminary Report on Patentability of the ISA dated Apr. 22, 2008 for PCT/CA2006/000364; 1 page.

Supplementary European Search Report for dated Nov. 25, 2008, for European Application No. EP 06705316.5, published as PCT/CA2006/000364, 7 pages.

European Official Communication dated Mar. 20, 2009 for European Application No. EP 06705316.5, based on PCT/CA2006/000364, 4 pages.

Response to EP Official Communication dated Mar. 20, 2009 for PCT App. No. PCT/CA2006/000364; filed on Dec. 23, 2009; 8 pages.

Response to EP Official Communication dated Oct. 10, 2008 for EP07701832.3 based on PCT/CA2007/00314 and filed on Nov. 7, 2008; 4 pages.

Chinese Official Action (with English translation) dated Mar. 31, 2010, for CN 2007800071414; 5 pages.

U.S. PTO Notice of Allowance dated Jun. 28, 2010 for U.S. Appl. No. 12/090,717.

Response dated Jun. 25, 2010 to Chinese Official Action for Chinese Patent Application No. 2007800071414.4; 8 pages.

Eijkel et al.; "A dc Microplasma on a Chip Employed as an Optical Emission Detector for Gas Chromatography;" Analytical Chemistry; vol. 72, No. 11; Jun. 1, 2000; pp. 2547-2552.

Fay et al.; "Emission Spectrometric Method and Analyzer for Traces of Nitrogen in Argon;" Analytical Chemistry; vol. 34, No. 10; Sep. 1962; pp. 1254-1260.

Lefebvre et al.; "Excitation DE N$_2$, O$_2$ ET H$_2$, EN Impuretés Dans Des Décharges De Gaz Rares He Ne ET Ar;" Revue De Physique Appliquee; Tome 10; May 1975; pp. 137-142.

Leys; "A Method of Background Correction for Direct Reading Optical Emission Spectroscopic Trace Analysis Using Offset Exit Slits;" Analytical Chemistry; vol. 41, No. 2; Feb. 1969; pp. 396-398.

Ricard et al.; "Analyse qualitative d'impuretés dans l'helium par spectroscopie d'èmission;" Analysis; vol. 6, No. 7; Jan. 1978; 7 pages.

Rosenkranz et al.; "Development of an automated speciation analyzer;" American Laboratory; vol. 31, No. 20; Oct. 1999; pp. 17-18, 20-22, and 24.

Skogerboe et al.; "A Dynamic Background Correction System for Direct Reading Spectrometry;" Applied Spectroscopy; vol. 30, No. 5, Sep. 1976; pp. 495-500.

Svishchev; "A Modulator for the Automatic Subtraction of Continuous Background in Optical Spectrometers;" Optics and Spectroscopy; vol. 16, No. 2; Feb. 1964; pp. 184-186.

Walker; "Detector for trace amounts of nitrogen in helium;" Cryogenics; vol. 26, No. 11; May 1986; pp. 297-299.

Yu et al.; "An Optical Emission Study on Expanding Low-Temperature Cascade Arc Plasmas;" Plasma Chemistry and Plasma Processing; vol. 18, No. 4; Jan. 1998; pp. 461-485.

Badareu, et al., "Gaze ionizate (Ionized Gases)", Dunod Edition, 1968, Part 1, 166 pages.

Badareu, et al., "Gaze ionizate (Ionized Gases)", Dunod Edition, 1968, Part 2, 171 pages.

Kazantsev, et al., "Practical Spectroscopy of High Frequency Discharges", Pienum Press, 1998, ISBN 0-306-45676-1, pp. 7.

Bochkova, et al., Spectroscopic Analysis of Gas Mixtures, Leningrad State University Academic Press, 1965 SF-4101, Part 1, 88 pages.

Bochkova, et al., Spectroscopic Analysis of Gas Mixtures, Leningrad State University Academic Press, 1965 SF-4101, Part 2, 77 pages.

PCT Written Opinion dated Jun. 7, 2006; for PCT Pat. App. No. PCT/CA2006/000364; pp. 1-5.

* cited by examiner typical emission spectrum of pure Argon

Typical emission spectrum of pure Argon with 5 ppm $N_2$ added

Linearity curve of a binary mixture of $N_2$ in Argon

Emission spectrum of 5 ppm $N_2$ in Argon with moisture added

Effect of various levels of moisture on $N_2$ emission lines of a 5 ppm $N_2$ in Argon sample Effect of various levels of moisture on the background emission spectrum of a mixture of 5 ppm $N_2$ in Argon sample Calibration of the 337 nm band height* in function of the added nitrogen concentration Emission spectrum of 5 ppm 5 ppm $N_2$ in Argon sample with $O_2$ added to the sample Emission spectrum of a mixture of 5 ppm $N_2$ in Argon with $H_2$ added to the sample Emission spectrum of a mixture of 5 ppm $N_2$ with $CH_4$ added

FUNCTIONAL BLOCK DIAGRAM OF
THE PROPOSED PLASMA EMISSION BASE SYSTEM

INTERFERENCE TESTING SETUP

FUNCTIONAL BLOCK DIAGRAM OF THE PROPOSED PLASMA EMISSION BASE SYSTEM, WITH REFERENCE CELL

SYSTEM AND METHOD OF ELIMINATING INTERFERENCE FOR IMPURITIES MEASUREMENT IN NOBLE GASES

CROSS REFERENCE TO RELATED APPLICATIONS

This application is a National Stage Application under 35 U.S.C. §371 of International Application number PCT/CA2007/000314 filed on Feb. 28, 2007 which, along with the subject National Stage Application, claims the benefit of U.S. Provisional Application No. 60/776,921 filed Feb. 28, 2006 under 35 U.S.C. §119(e).

FIELD OF THE INVENTION

The present invention generally relates to fluid analytical systems and methods for measuring impurities in a gas background. It more particularly concerns a system and a method of eliminating interference, stabilizing and linearizing on line plasma or discharge type emission based detector for impurities measurement in noble gases.

BACKGROUND OF THE INVENTION

In the air separation industry or in the field of the electronic industries, many different types of high purity gases must be analyzed for quality or process control. To achieve this, there are several types of analytical instruments available on the market using different types of detectors.

Some of these detectors are specific to an impurity to be measured and their levels of susceptibility to other impurities present in the sample can be acceptable since they do not affect dramatically the accuracy of the measurement. An example of such a detector known in the art is the $O_2$ fuel cell detector used to measure $O_2$ impurities in gas samples. The presence of $H_2$, $N_2$, $H_2O$ or $CH_4$ in about the same level of the $O_2$ to be measured does not interfere with the $O_2$ identification and quantification.

The measurement of Hydrocarbons by a standard configuration flame ionization detector (FID) is another example of this. The FID will not be really affected by other traces of impurities in presence in the sample like $O_2$, $N_2$, CO, $CO_2$ or moisture. Thus, in such detector configurations no special consideration has to be taken to protect them against such undesirable interference.

Typical online analytical systems rely on detector that uses the chemical or physical properties of the impurity to be measured to generate an electrical signal. However, when the impurity to be measured is inert at ambient condition, such detector could not be used. A good example of this is the measurement of traces of $N_2$ in Argon or Helium. The inertness of $N_2$ makes it difficult to be measured at low levels. Researchers have chosen the spectroscopic emission method in the early age of the industrial analytical equipments to measure it. This method is generally known as plasma emission detection and is used with sample background gases that are easy to ionize with the help of electrical or electro magnetic field generator. An early spectroscopic emission system for the $N_2$ in Argon measurement is described in "Spectroscopic analysis of gas mixtures", O. P. Bochkova and E. Y A. Shreyder, Leningrad State University Academic Press, 1965 SF-4101. This concept, introduced more than 50 years ago, is still in use today.

The basic concept of this system is to get a discharge through the gas to create plasma, i.e. a gaseous ionized zone. The molecules of the background gas get excited and excite the gas molecules of $N_2$ impurities which in turn emit various spectral emission wavelengths characteristic of $N_2$. A common application of this concept is the measurement of $N_2$ in Argon or Helium sample. Such technology used in this system is known as emission spectroscopy. The molecular species in the vapour phase is excited to emit light, then, the spectrum and the intensity of the emitted light are analyzed to determine the concentration of impurity in the sample.

The excitation of an atom or a molecule to a level that can emit photons requires energy greater than or equal to the excitation energy of a given level. This energy can be supplied by conversion of the kinetic energy of electrons (electrons temperature), ions or atoms colliding, absorption of light quanta and collisions of second kind. However, the later refers to radiation-less transfer of excitation energy from other particles.

In the art, almost all possible ways to create plasma and to excite the sample background (Ar or He) have been experimented for the determination of $N_2$. The excitation ranges from direct DC or AC current discharge through the gas, the simplest form of excitation, to micro-wave induced discharge or plasma, passing by the low frequency silent electric discharge and VHF-RF frequency range. The operating pressures are also variable, ranging from low pressure, i.e. rough vacuum operating emission cell, to the atmospheric pressure. Depending on excitation mode, some discharges are of a glow type, like in low pressure, and others are of a silent electric discharge type, also called dielectric barrier discharge (DBD) or streamer discharge. This type of discharge occurs at atmospheric pressure. The power coupling technique used in the above spectroscopic emission systems, also differs. The direct coupling method is referred to a configuration where the metal electrodes are in contact with the gas to be ionized.

Such systems are described in U.S. Pat. Nos. 3,032,654; 5,412,467; 4,148,612 and 5,168,323, and in the following papers: "Spectroscopic analysis of gas mixtures", O. P. Bochkova and E. Y A. Shreyder, Leningrad State University Academic Press, 1965 SF-4101: "Excitation de l'azote, oxygène et hydrogène en impuretés dans des décharges de gaz rares He, Ne et argon", A. Ricard, J. Lefebvre, Revue de physique appliquée, 10 mai 1975 tome 10; "Detector for Trace Amount of Nitrogen in Helium", R. J. Walker, Cryogenics, 1986, vol. 26 May; "A DC Microplasma on a chip employed as an optical emission detector for gas chromatography", Jan C. T. Eijkel et Al., Analytical Chemistry vol. 72, No. 11 Jun. 1, 2000; "An Optical Emission Study on Expanding Low Temperature Cascade Arc Plasmas", Q. S. Yu and H. K. Yasuda, Plasma chemistry and plasma processing Vol. 18, No. 4, 1998, and "Emission Spectrometric Method and Analyzer for Trace of Nitrogen in Argon", Homer Fay, Paul H. Mohr, and Serard A Cook, Linde Co. Division of Union Carbide, Analytical Chemistry, Vol. 34, No. 10 Sep. 1962.

In all of these abovementioned references, it can be seen that for the $N_2$ measurement, the emission wavelength typically used for low level measurement is 337.1 nm. However, 391 nm is sometimes used when sample background is Helium because of its strong intensity compared to other $N_2$ emission lines or bands. This leads to the fact that in all the commercially available systems known today using emission spectroscopy to measure $N_2$ in Ar, spectral emission at 337.1 nm is used to identify and quantify $N_2$. When background is Helium, emission at 391 nm is preferred.

The wavelength of interest is filtered out by means of interference filters, grating or monochromator and its intensity is transformed into an electrical signal by any suitable photo electrical device. The electrical signal is then processed to provide the final $N_2$ level.

Most of these systems use a single emission cell with a single optical measurement channel. It is a general belief that measuring $N_2$ emission of an excited Argon or Helium plasma will give a linear signal from sub ppm to a few hundred ppm and no special means is generally used to correct any nonlinearity.

However, even if the above-described method is generally accepted by people involved in the art for $N_2$ measurement, this method could become unreliable under certain conditions that are found in almost all industrial field applications. Indeed, the ideal situation would be to have a dry binary mixture of $N_2$ in Ar or He. In such case, the measurement will not be affected by any other impurities. But even in such conditions, non-linearity occurs, as it will be described and demonstrated thereinafter, thereby resulting in substantial measurement errors.

As another example, in air separation industries, the $N_2$ level in Argon products should be measured. Based on a particular Ar production process, many other impurities could also be present in the Ar and sometimes at a higher level than $N_2$. Typical impurities generally found are: $H_2$, $O_2$, $N_2$, $CH_4$, CO and $H_2O$. Furthermore, at the truck loading station, when the Ar is transferred into the tanker to be shipped to the customer, ambient air and moisture contamination is a to frequent problem. There is also the fact that, at the present time, customers of such produced high purity Argon are demanding more rigorous quality control. As consequence, customers are also asking for the measurement of other impurities like $CO_2$ and NMHC (Non Methane Hydrocarbons), leading to believe that these impurities could also be present as an impurity in the high purity Argon.

In these situations, the presence of other impurities will have an effect on the system's performance. $N_2$ and Ar are inert gases and normally do not react with other molecules at ambient conditions. However, inside a plasma emission system, gases under ionization state (or plasma) are a very reactive and aggressive medium. Many call it the forth state of matter, as described in "Gaze Ionizate (ionized Gases)", M. M. Badareu and Popescu, Dunod Edition. It has been known for a long time that in an ionized gas or plasma, many chemical reactions can occur even with inert gases. Plasma contains molecule radicals and atoms but also ions and free electrons which result from the coupling of energy with matters in the gaseous state. This application field relates to plasma chemistry and plasma processing.

In this field, many research works have been conducted with plasma systems similar to the ones used in analytical systems today used. Most of them use DBD or Dielectric Barrier Discharge (also called silent dielectric discharge) because of its simplicity. Thus, it is relatively inexpensive to manufacture compared to systems relying on other modes of excitation. RF excited discharge or pulse and direct current generating discharge or plasma could also be used. In this field of application, the "reactor" property of plasma is used to trigger various chemical reactions. People involved in this art have documented and reported many species, free radical and their reaction rates. They use emission spectroscopy to diagnostic or investigate plasma reactor operations.

Since most of plasma reactors used is very similar, not to say the same, as the emission cell used in the commercially available analytical instruments, they should trigger different types of chemical reactions if there is different types of impurities flowing in it. Despite this fundamental evidence it seems that, in the analytical instruments used today, no special considerations are taken to overcome interference problems.

As mentioned above, even if the previously described systems perform relatively well in the case of a dry binary mixture, except for the system linearity, it can be seen from the above that, in the real word, many other impurities could be present in the gas to be analysed, thereby leading to inaccurate measurement of the impurities to be measured. Moreover, as also mentioned above, the methods presently used today could become unreliable under particular conditions surrounding the emission system and additional impurities that could be present in the gas under analysis.

It would therefore be desirable to provide an improved method and an improved system for measuring impurities such as $N_2$ in rare and noble gases that would be very accurate and reliable, whatever the surrounding conditions and the additional impurities that could be present in the gas under analyse. Moreover, it would be even more desirable to provide such a method that would provide accurate measurements even at sub-ppb and up to 10,000 ppm levels while providing a long-term stability.

SUMMARY OF THE INVENTION

An object of the present invention is to provide a method and a system of eliminating interference for impurities measurement in rare and noble gases that satisfies the above-mentioned needs.

Accordingly, the method of the present invention mainly relies on the use of a combination of particularly designed means serially connected for cancelling interferences. Proper means for correcting linearity issues are also advantageously implemented.

More particularly, the invention provides a method of eliminating interference for impurities measurement in noble gases, comprising steps of:
a) providing a gas sample having interfering impurities and an impurity to be measured therein;
b) providing a plurality of trapping means serially connected to define an impurities trap having an inlet and an outlet, each of the trapping means being adapted to trap a specific one of the interfering impurities without affecting the impurity to be measured;
c) introducing the gas sample at the inlet of the impurities trap for removing the Interfering impurities;
d) adding moisture to the gas sample at the outlet of the impurities trap;
e) introducing the gas sample in a plasma cell of a plasma emission system;
f) collecting an emission light generated by the plasma cell at a specific emission wavelength not subjected to spectral interference for providing an emission signal representative of a concentration of the impurity to be measured of the gas sample; and
g) measuring the concentration of the impurity to be measured according to the emission signal provided in step f).

In a preferred embodiment, the gas sample comprises argon and the impurity to be measured comprises nitrogen. In a further preferred embodiment, in the step f), the specific emission wavelength is 357.69 nm.

In another preferred embodiment, the method further comprises, before step e), a step of adding oxygen to the gas sample at the outlet of the impurities trap.

In another preferred embodiment, each of the trapping means are adapted to trap at least one of $H_2O$, $O_2$, $CH_4$, CO, $CO_2$, $H_2$, organic compounds and non-methane hydrocarbon impurities.

In another preferred embodiment, the method further comprises a step of isolating the plasma cell from surroundings.

In another preferred embodiment, the method further comprises, before step g), steps of:

collecting a background emission light generated by the plasma cell at an emission wavelength neighbouring the specific emission wavelength for providing a background emission signal; and subtracting the background emission signal from the emission signal to provide a net emission signal representative of the net emission of the impurities to be measured, thereby cancelling background variations.

Preferably, the method further comprises steps of:

measuring a plasma pressure of the plasma cell; and compensating the emission signal representative of the concentration of the impurity to be measured according to the plasma pressure.

Advantageously, the method further comprises a step of compensating a non-linearity of the emission signal. This step can be achieved by adjusting a driving power of the plasma cell according to the concentration of the impurity to be measured, or by applying a correcting algorithm dependent on the concentration of the impurity to be measured.

In another preferred embodiment, the method further comprises steps of:

providing a reference plasma cell connected in parallel with the emission cell for generating a reference emission light representative of a concentration of the impurity to be measured;

processing the reference emission light for providing a level of the concentration of the impurity to be measured; and adjusting a driving power of the plasma cell according to the level of the concentration of the impurity to be measured.

The method of the present invention, when implemented with most of the above-mentioned preferred features, is particularly advantageous since it offers long-term stability while providing very accurate and reliable results, even at subs ppb and up to 10,000 ppm levels, whatever the surrounding conditions and the additional impurities that could be present in the gas under analyse.

Another object of the present invention is to provide a system of eliminating interference for impurities measurement in a gas sample having interfering impurities and an impurity to be measured therein. The system comprises:

a plurality of trapping means serially connected to define an impurities trap having an inlet and an outlet, each of the trapping means being adapted to trap a specific one of the interfering impurities without affecting the impurity to be measured;

means for adding moisture to the gas sample, the means being serially connected to the outlet of the impurities trap;

a plasma cell of a plasma emission system serially connected to the means for adding moisture for generating an emission light representative of a concentration of the impurity to be measured of the gas sample; and processing means operatively connected to the emission cell for processing the emission light and providing the concentration of the impurity to be measured.

In a preferred embodiment, the plurality of trapping means comprises a molecular sieve for trapping $H_2O$ impurities, a reduced copper based catalyst for trapping oxygen impurities, a palladium based catalyst for trapping hydrogen impurities, a nickel based catalyst for trapping CO, $CO_2$ and non-methane hydrocarbon impurities, and an activated carbon based catalyst for trapping organic compounds.

In another preferred embodiment, the system is further provided with means for adding oxygen to the gas sample, the means being serially connected to the outlet of the impurities trap.

In another further preferred embodiment, the system is further provided with an insulating enclosure mounted around the plasma cell for insulating the plasma cell from surroundings.

In another further preferred embodiment, the processing means are provided with collecting means for collecting the emission light at a specific emission wavelength not subjected to spectral interference to provide an emission signal representative of a concentration of the impurity to be measured. The processing means are further provided with a microprocessor for processing the emission signal and providing the concentration of the impurity to be measured.

Preferably, the processing means is further provided with background collecting means for collecting a background emission light generated by the plasma cell at an emission wavelength neighbouring the specific emission wavelength to provide a background emission signal. The microprocessor is adapted for subtracting the background emission signal from the emission signal to provide a net emission signal representative of the net emission of the impurity to be measured, thereby cancelling background variations.

Still preferably, the processing means are further provided with a correcting algorithm for compensating a non-linearity of the emission signal according to the concentration of the impurity to be measured.

In a further preferred embodiment, the system is advantageously provided with a reference plasma cell connected in parallel with the emission cell for generating a reference emission light representative of a concentration of the impurity to be measured. The processing means are adapted to process the reference emission light for providing a level of the concentration of the impurity to be measured. The system further has adjusting means for adjusting a driving power of the plasma cell according to the level of the concentration of the impurity to be measured.

BRIEF DESCRIPTION OF THE DRAWINGS

These and other objects and advantages of the invention will become apparent upon reading the detailed description and upon referring to the drawings in which.

While the invention will be described in conjunction with example embodiments, it will be understood that it is not intended to limit the scope of the invention to such embodiments. On the contrary, it is intended to cover all alternatives, modifications and equivalents as may be included as defined by the present description.

DESCRIPTION OF PREFERRED EMBODIMENTS

As previously mentioned, having a look at different emission spectrums generated by plasma source using different excitation modes reveals that emission line wavelengths for $N_2$ impurities are the same.

Below, are reported the results of our investigations that were conducted to enlighten the problems encountered when attempting to measure $N_2$ in presence of some other impurities, with emission spectroscopy. Then, a new method and a new system overcoming these problems will be described.

These investigations were conducted with a prior art plasma emission system used to measure $N_2$ in Argon. But it is worth mentioning that the following discussion could also be applied to $N_2$ in He, Ne or Krypton. The emission system tested here was working at atmospheric pressure and excitation frequency ranging from 60 Hz to 4 MHZ. Excitation field could also be modulated. Emission spectrum looks almost the same for all excitation frequencies except for the intensity and noise. Lower excitation frequency dielectric barrier discharge has low emission intensity and is noisier due to spatial movement of streamers. Higher frequency looks more like a glow discharge type than streamer type emission, intensities being higher and noise being lower. Nevertheless, in almost all cases emission wavelength for a particular impurity is the same.

Figure 1:
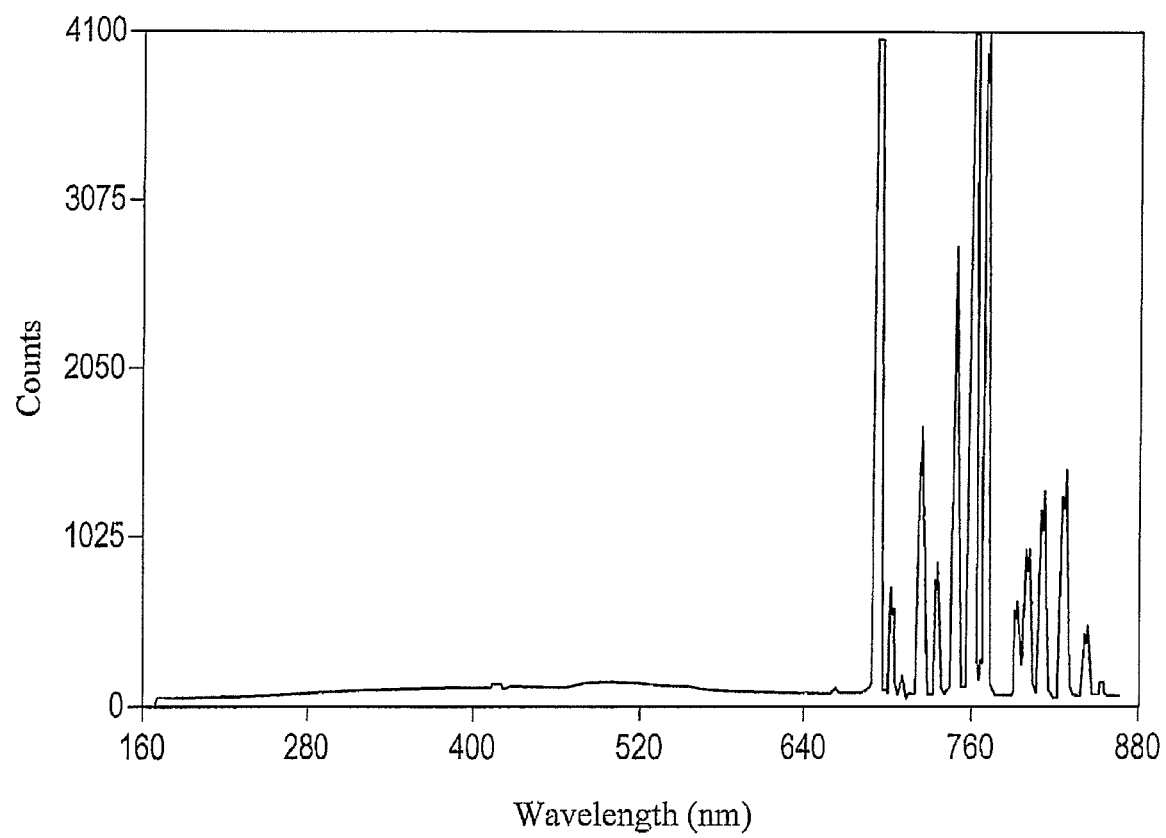
FIG. 1 shows a typical emission spectrum of pure Argon.
Figure 2:
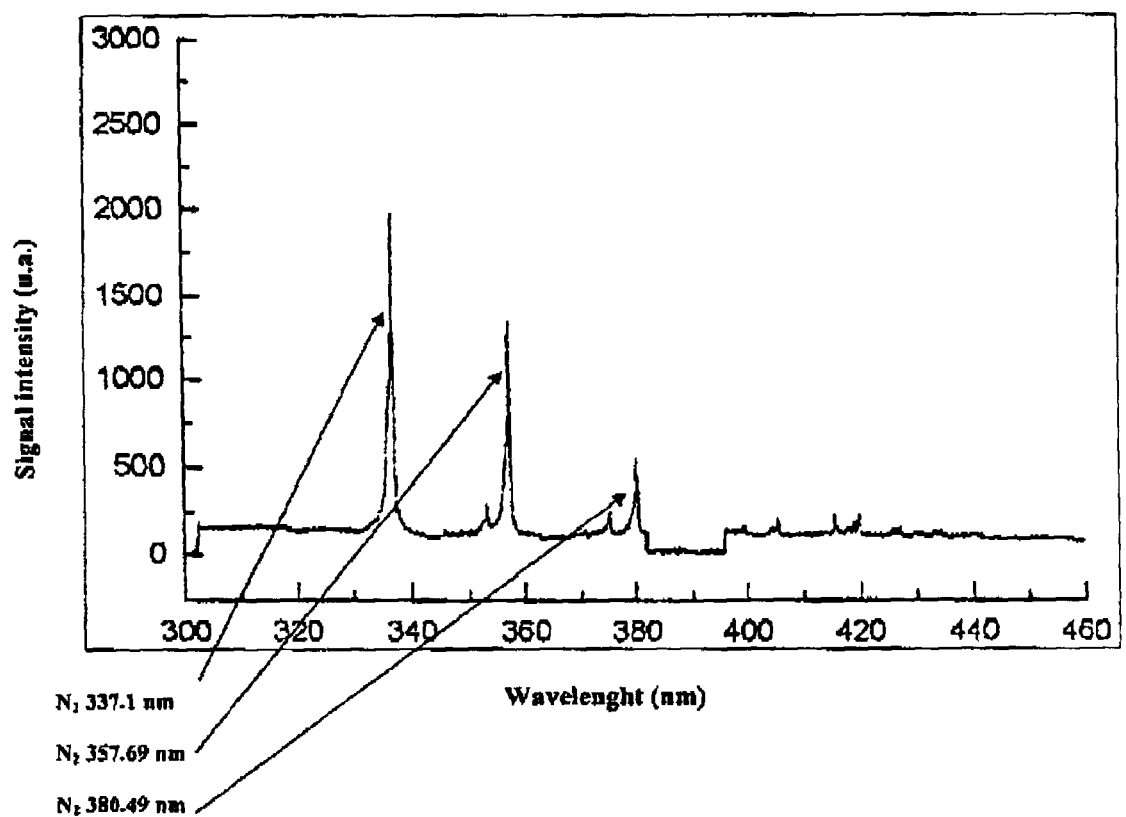
FIG. 2 shows a typical emission spectrum of pure Argon with 5 ppm $N_2$ added therein.
Figure 3:
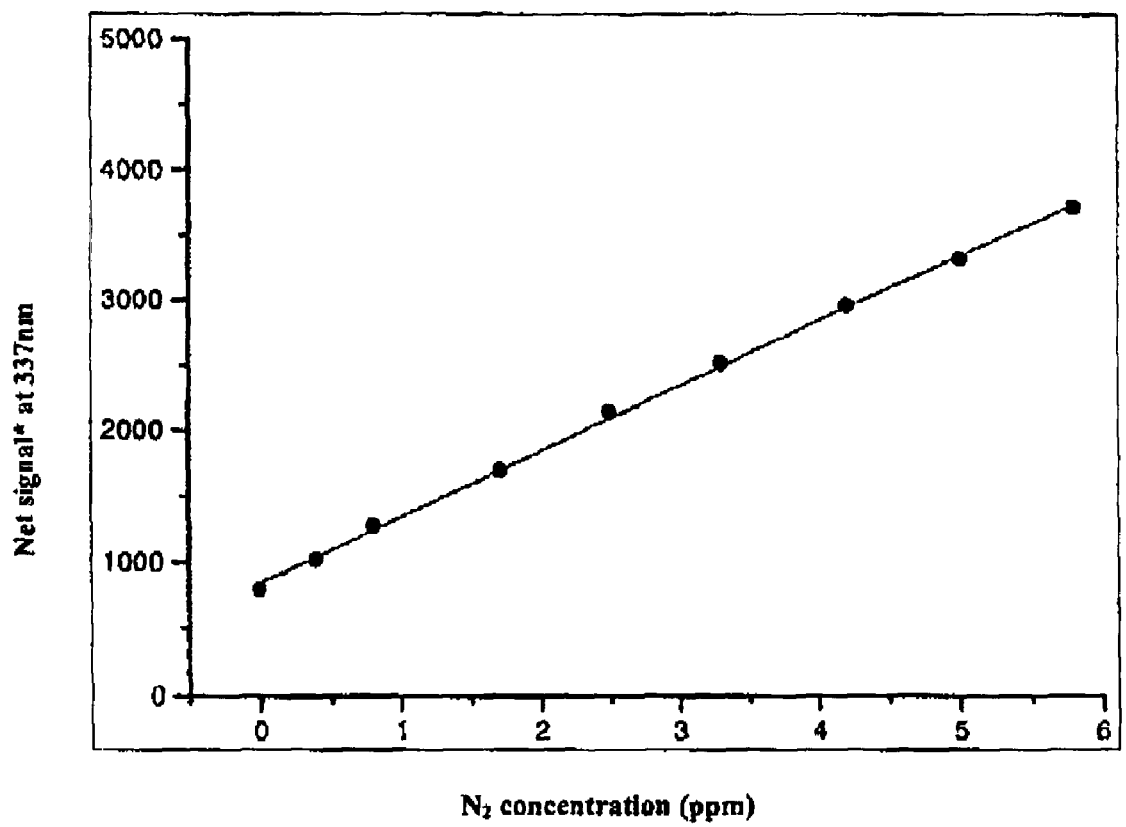
FIG. 3 shows a linearity curve of a binary mixture of $N_2$ in Argon.

Referring to FIG. 1, there is shown a typical emission spectrum of a pure Argon sample, which is an Argon sample having less than 1 ppb total impurity therein. FIG. 2 shows the typical emission spectrum of the same Argon sample, wherein 5 ppm $N_2$ have been added. Typical $N_2$ emission wavelengths could be easily seen. Clearly, the 337.1 nm emission is the most intense. FIG. 3, as for it, shows a typical linearity curve from the ideal case, i.e. a binary mixture of $N_2$ and Argon only, without any other impurities.

The above-described Figures are not subject to any interference and represent the ideal conditions. However, hereinbelow is described what could happen in real applications where there is not only $N_2$ impurities in presence into the emission cell system.

Interference Problems:

a) Moisture interference: As previously mentioned, in air separation plants, one of the common impurities is moisture. Moisture could be present at various levels, depending on surrounding conditions such as where the sample is coming from. Typically, at truck loading stations, the moisture level could be higher due to atmospheric contamination during sample manipulation.

Figure 4:
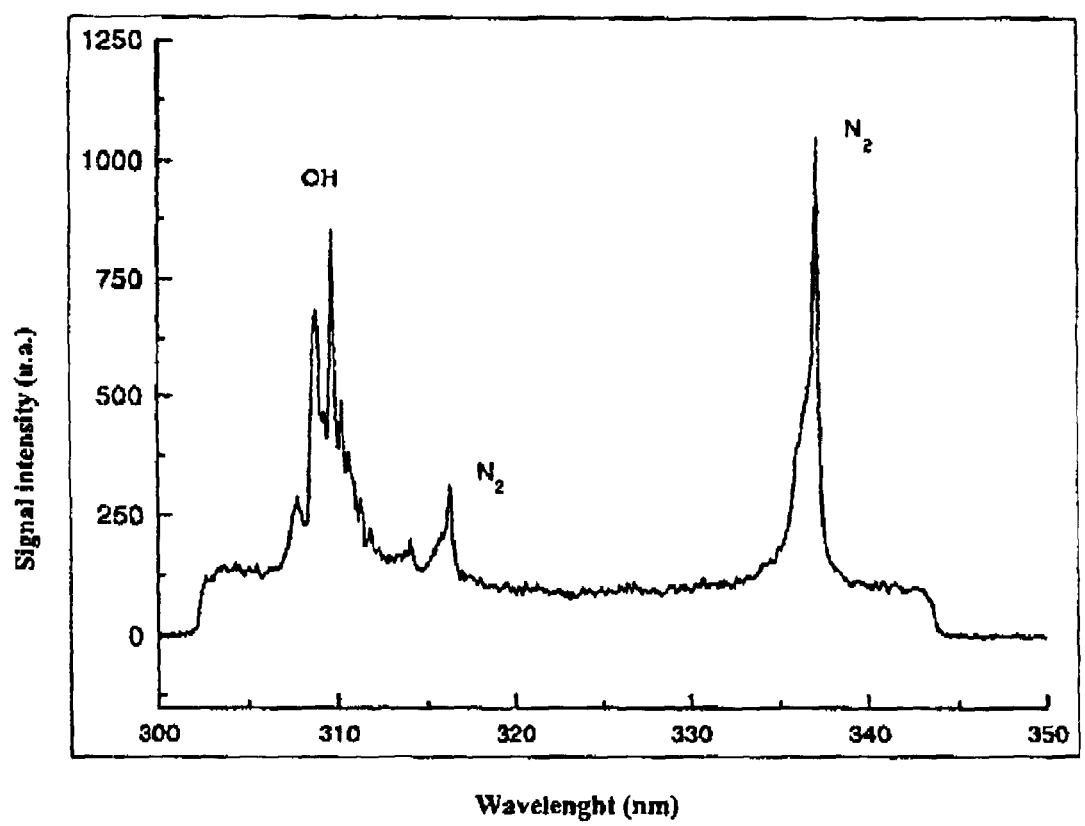
FIG. 4 shows a typical emission spectrum of 5 ppm $N_2$ in Argon with moisture added therein.
Figure 5:
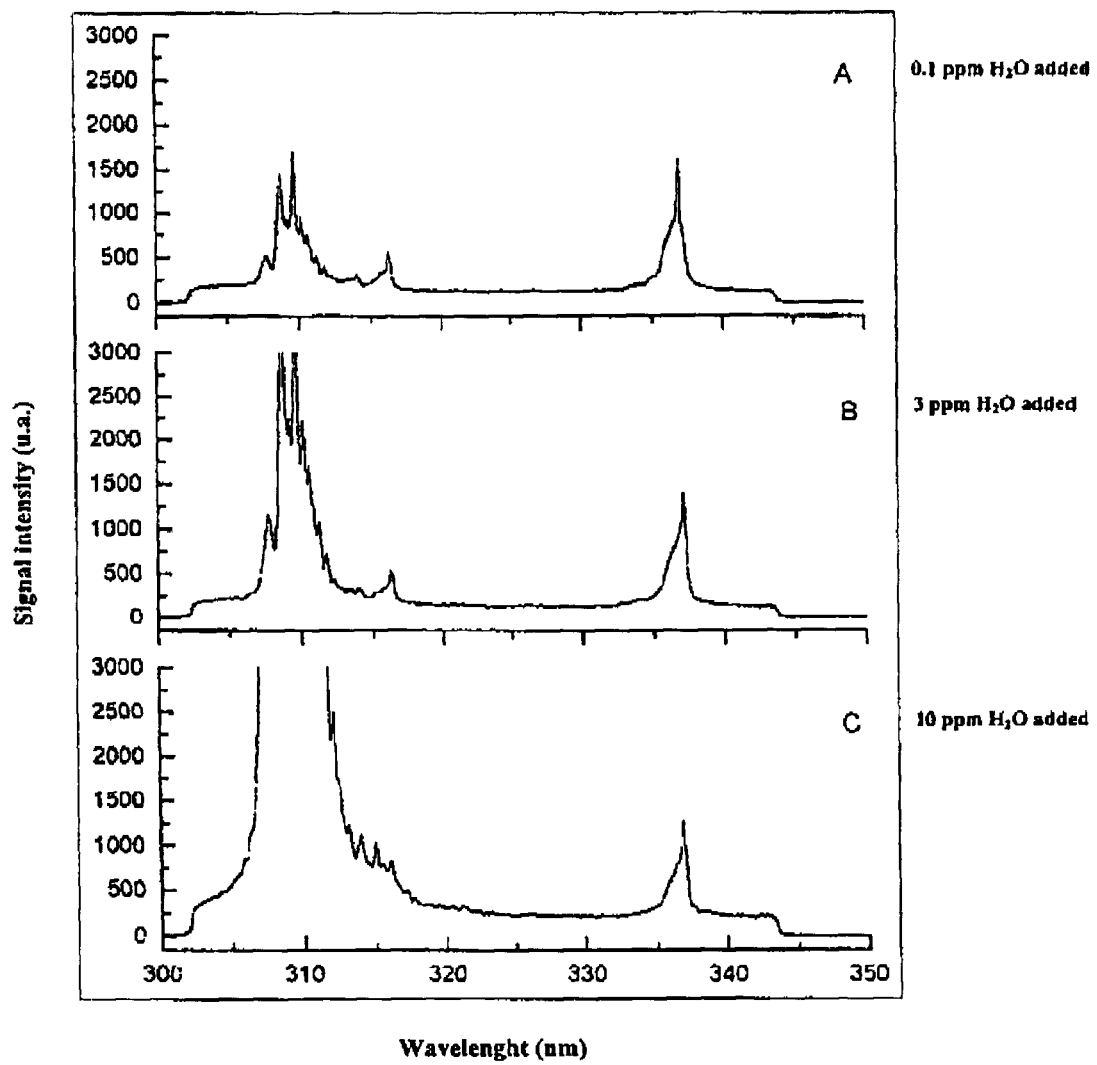
FIGS. 5A to 5C show typical emission spectrums of a 5 ppm $N_2$ in Argon sample, with different levels of moisture added therein.

In the attempt of finding the influence of moisture on Nitrogen determination, some moisture was added to the previous sample of binary mixture of 5 ppm $N_2$ in Argon. FIG. 4 shows the emission spectrum which was thus obtained. As it can be seen, the presence of moisture substantially reduces the Intensity of the $N_2$ emission at 337.1 nm. Adding the same amount of moisture once again to the sample will again contribute to the decreasing of the intensity of $N_2$, but not as much. So, moisture effect is non linear. This later fact can be seen in FIGS. 5A to 5C, wherein three different levels of moisture contamination on $N_2$ emission are compared. By repeating these experiments, it can be concluded that, after increasing the level of moisture over a certain value, the effect of such moisture contamination on $N_2$ emission at 337.1 nm is much less pronounced.

Figure 6:
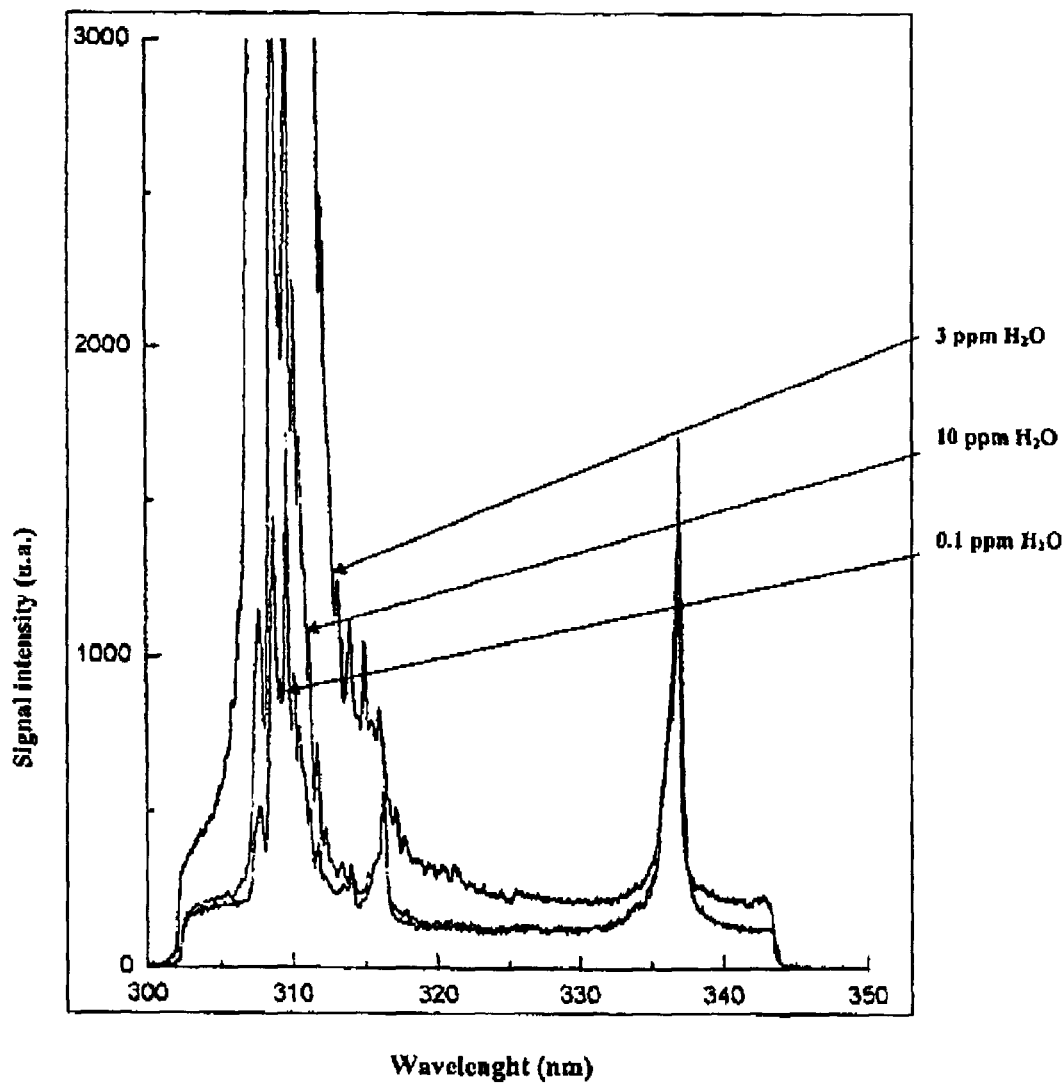
FIG. 6 shows typical emission spectrums of a 5 ppm $N_2$ in Argon sample, with different levels of moisture added therein.

Referring now to FIG. 6, which shows the effect of different levels of moisture on the background emission spectrum, it can be seen that the continuum or background emission spectrum is increasing with the level of moisture. Moreover, by looking at the various emission spectrums, the emission of OH can be seen between 302 to 309 nm.

Figure 7:
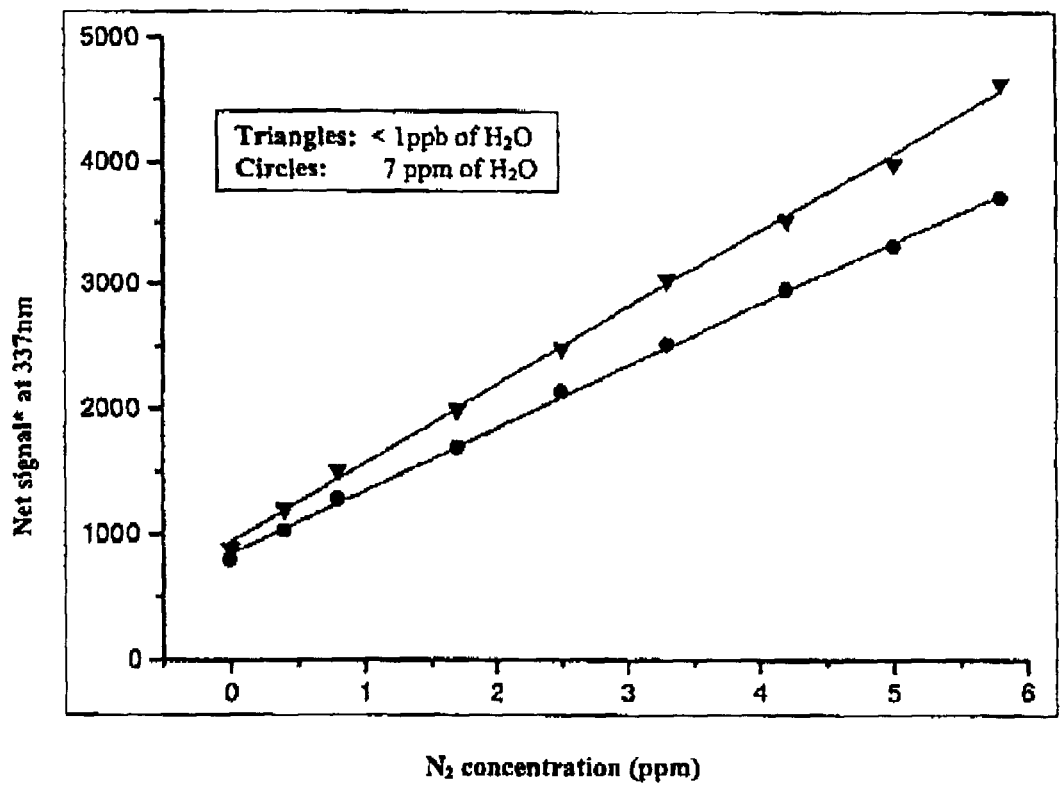
FIG. 7 shows linearity curves of a 5 ppm $N_2$ in Argon sample, with different levels of moisture added therein.

Reference is now made to FIG. 7 which shows the typical response signal linearity with and without moisture, the latter case having already been illustrated in FIG. 3. Clearly, one can easily see that the presence of moisture in the sample leads to an under estimation of the $N_2$ value.

It should be noted that the interference caused by moisture is more of a physical/chemical type than of a spectral type in the sense that there is no emission line caused by moisture close to the $N_2$ emission line. However, since that, in a plasma system, there is a competition between various species in presence for the energy available, which is mostly supplied by the Argon in the metastable state, it results that the impurities having the lowest ionization potential will be favoured because they react faster with the Argon metastable, thereby reducing the excitation efficiency for the $N_2$. Moisture has a lower ionization potential. This is shown by the emission spectrum. Indeed, an increase of moisture results in a higher intensity of OH emission while $N_2$ emissions are going down.

As previously described, in "Development of a Detector for Ultratrace Nitrogen in Argon using Low-Pressure Capillary Glow Discharge Molecular Emission Spectrophotometry", Hiroshi Ogino et Al., Anal-Chem. Vol 69, No 17, September 1997, Ogino et al. have also noticed the same type of interference caused by moisture, i.e. decreased sensitivity and higher background emission in presence of moisture. They also report that moisture does not cause any spectral interference.

Figure 8:
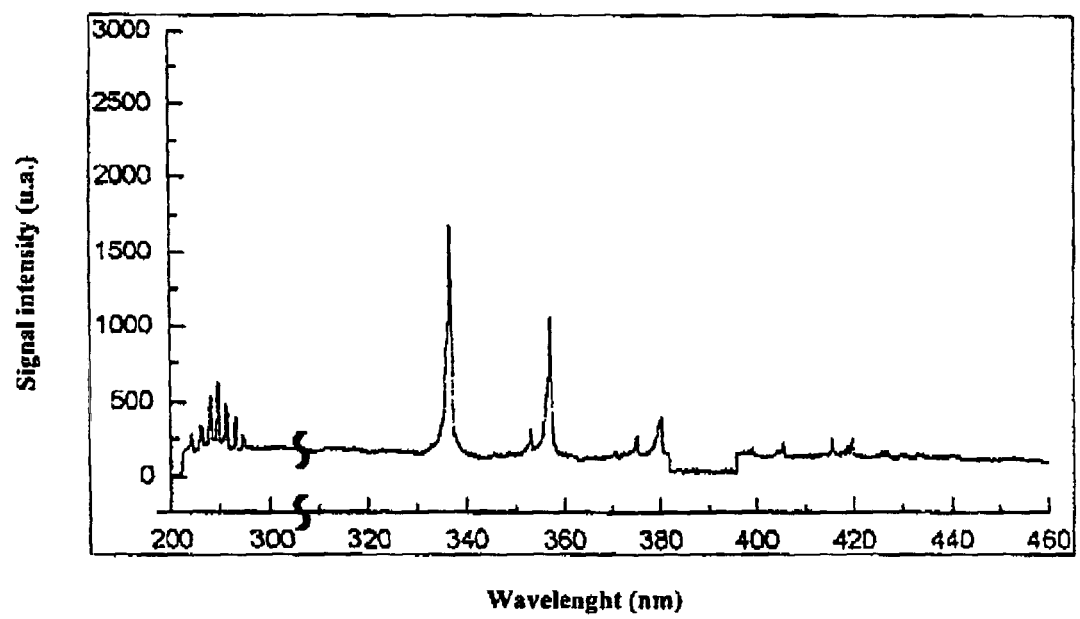
FIG. 8 shows a typical emission spectrum of 5 ppm $N_2$ in Argon with $O_2$ added therein.
Figure 9:
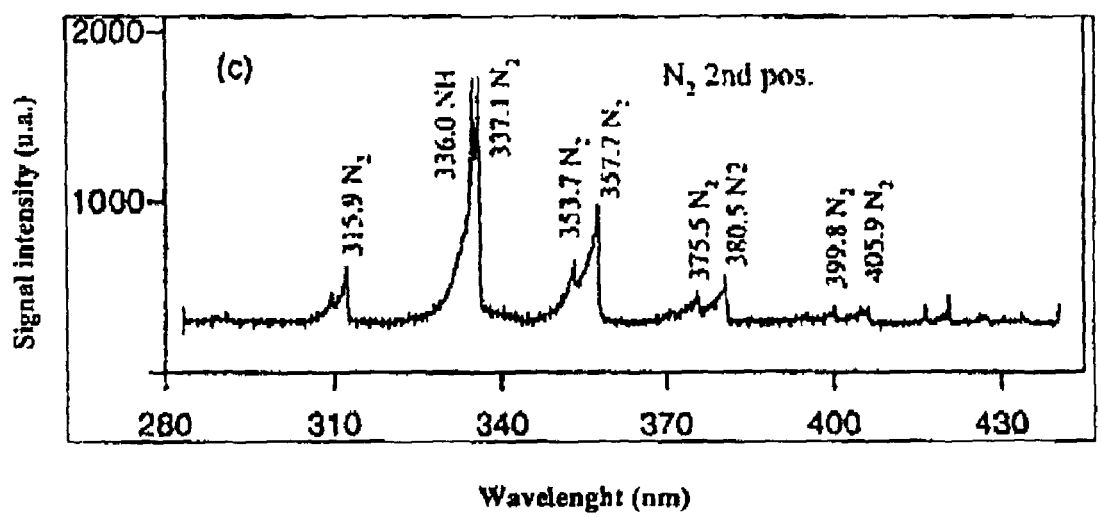
FIG. 9 shows a typical emission spectrum of 5 ppm $N_2$ in Argon with $H_2$ added therein.
Figure 10:
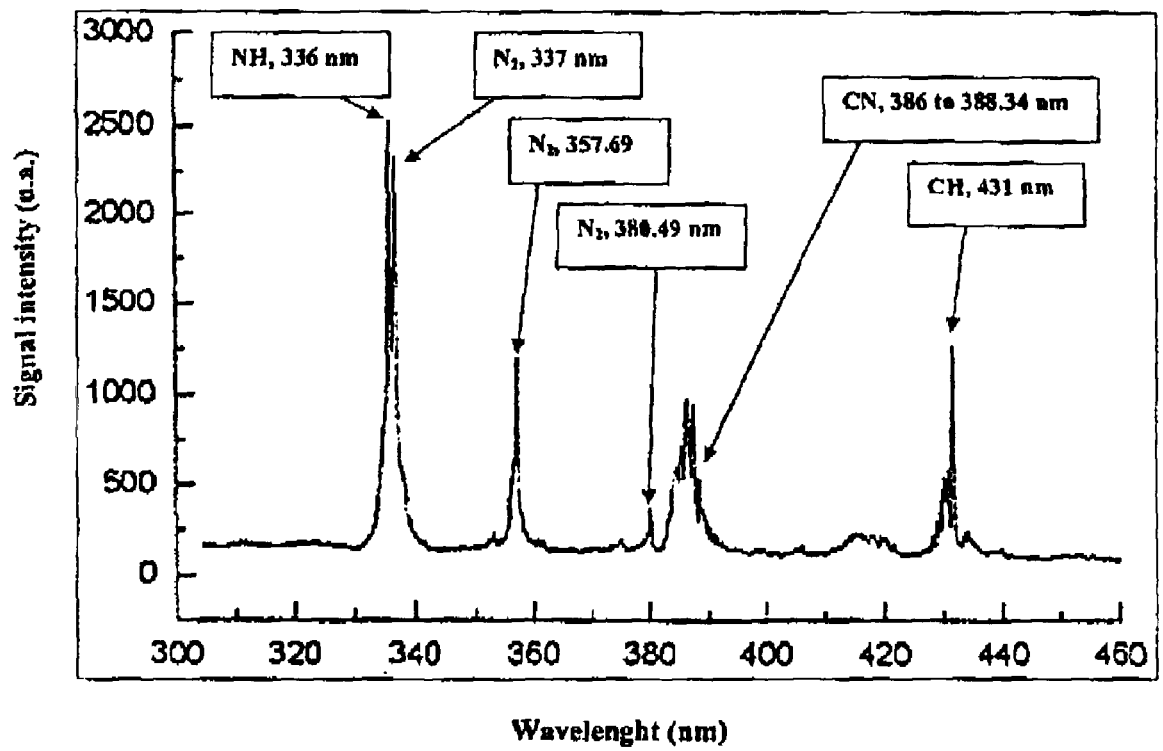
FIG. 10 shows a typical emission spectrum of 5 ppm $N_2$ in Argon with CH4 added therein.

Therefore, it can be concluded without any doubt that moisture in a sample of $N_2$ in Argon will result in physical/chemical interference that will lead to measurement errors, regardless of the excitation mode which is used. The presence of one impurity affects the other and vice versa.

b) $O_2$ interference: The effect of $O_2$ impurity on $N_2$ measurement in an Argon sample has also been investigated. When some $O_2$ is added to a mixture of 5 ppm $N_2$ in Argon, emission of NO between 200 and 300 nm appears, as illustrated in FIG. 8. This proves that Nitrogen and Oxygen react together. Once again, this interference is of a physical/chemical type. The $N_2$ reacting with the $O_2$ is no longer available to generate the emission wavelength at 337.1 nm since a part of $N_2$ impurity is "consumed". Thus, the emission wavelength intensity of $N_2$ decreases. Again, this leads to an under estimation of the $N_2$ level when $O_2$ is present in the sample. It should however be noted that there is no spectral interference.

c) $H_2$ interference: Referring now to FIG. 9, the addition of $H_2$ in a 5 ppm $N_2$ in Argon sample results in a different type of interference based on plasma excitation mode. At low excitation frequency, no $H_2$ emission occurs. However, there is a spectral interference caused by the NH emission at 336 nm. Since the $N_2$ is generally measured at 337 nm, the emission at 336 nm will pass through the optical filter that has a bandwidth of about 3 nm. Even worst, the NH also has an emission at 337 nm as $N_2$ does. This causes a direct spectral Interference that cannot be eliminated with an interference filer. So, the signal generated by the photoelectric measuring device will take these interference emissions into account. Thus, in this case, the interference results in an over estimation of $N_2$ level since the reading will be higher than it is supposed to be. The possible source of $H_2$ contamination will be explained thereinafter.

d) $CH_4$ interference: Referring now to FIG. 10, $CH_4$ interference was also investigated with a binary mixture of 5 ppm $N_2$ in Argon wherein $CH_4$ was added. The resulting interference is substantially the same as the ones of $H_2$, i.e. there is emission lines caused by NH at 336 nm and at 337 nm, thereby resulting in direct spectral interference. In fact, there is dissociation of $CH_4$ and some part of the Hydrogen released reacts with the Nitrogen from the sample. The emission spectrum also shows the emission caused by CN between 386 to 388 nm and CH emission line also appears at 431 nm.

$CH_4$ is generally present in cryogenically produced Argon. It normally comes from the air incoming to the plant and it is not stopped by the process.

Some Argon plants use a warm Argon cycle to remove the Oxygen from the Argon. In this process there is generally a Palladium catalyst operating at high temperature, where $H_2$ is added to the crude Argon process stream. $CH_4$ could be generated in this catalyst bed due to the presence of other impurities in the process stream. The warm Argon cycle process generates high temperature steam. In the case of process upset that leads to unstable operation of the Palladium catalyst bed, impurities like moisture, Oxygen, Hydrogen and Methane could end up in the pure Argon column and then in the final product. In both cases, the $N_2$ level is measured by on line emission spectroscopy.

In the electronic field industries like the so-called "wafer fab", the use of a getter alloy base purifier is mandatory to get impurity levels below the single digit ppb. The first impurity to break through is the $N_2$. So, the monitoring of $N_2$ level is a good indication of the end of life of such purifier. However, when such purifier is close to its end of life, it is not uncommon that $H_2$ be released from the getter alloy. The monitoring range for $N_2$ level is generally below 10 ppb. The $H_2$ released will make the $N_2$ analyzer read higher, leading to replace the expensive alloy before its time.

e) Multi-component case interference: In "Analyse qualitative d'impuretés dans l'hélium par spectroscopic d'émission", A. Ricard and J. Lefebvre, Analysis, 1978 V.6, No. 7, pp. 299 to 305, the authors have identified the emission lines for $H_2$, $O_2$, $N_2$, $CH_4$ in a Helium plasma at atmospheric pressure. They also analyze various impurity effects on the other ones. They came to the conclusion that it is not possible to do an accurate measure of $N_2$ when there are other impurities in the sample. This is caused by the fact that these impurities do not have the same efficiency to de-excite the Helium metastable. They suggest the use of a chromatographic column to separate each of the impurities or to use a binary mixture. As previously explained, the later case is not possible in the industrial field.

The same problem complexity was also well explained in U.S. Pat. No. 4,801,209 entitled "Process and apparatus for analyzing a gaseous mixture and a visible emission spectrum generator therefor" and granted to Waldow. In this patent, Waldow clearly indicated that the emission spectrum emanating from a discharge within a mixture of gases is the sum of all photons being emitted with the result that the combined spectrum is not a linear sum of the individual spectrums.

The relative intensity of the spectral lines associated with the individual gases is not preserved due to what is known as the matrix effect. Deconvolution or separation of the individual spectrums from a combined spectrum is thus more of an art than a science. Complexity increases rapidly in multigas mixtures. The multi-component complexity problem is also discussed in "Spectroscopic analysis of gas mixtures", O. P. Bochkova and E. Y A. Shreyder, Leningrad State University Academic Press, 1965 SF-4101, at pages 149 and 199. They limited their analysis to a ternary mixture and found a very limited range of application. It should also be mentioned that their analysis was performed with high levels of impurities.

f) Specific interference of Argon in Helium: In "Analyse qualitative d'impuretés dans l'hélium par spectroscopie d'émission", A. Ricard and J. Lefebvre, Analysis, 1978 V.6, No. 7, pp. 299 to 305, the authors use the $N_2$ emission line at 391 nm. However, further to our advanced experiments, it was demonstrated that there is another source of strong interference when using this wavelength in Helium background. Indeed, only a minute diffusion of Argon into the Helium sample quenches almost completely the $N_2$ emission at 391 nm. The Argon comes back from ambient air diffusion. So, using this emission line for $N_2$ measurement in Helium in the industrial applications will be very risky, even if it is the most sensitive one.

g) Other interference sources affecting $N_2$ Quantification: Complete investigations on the combined effect of various impurities in a sample, i.e. when all the above-mentioned impurities are present in various levels in the sample, on the $N_2$ emission were not performed. However, the effect of the atmospheric pressure on the $N_2$ emission of a 100 ppb $N_2$ in Argon mixture was tested. The test conducted has shown that a variation of 30 inches of water shifts the reading anywhere between 20 to 30 ppb. A variation of 30 inches of water for the atmospheric pressure is about the variation between a sunny day and a day where there is a thunder storm. Since some applications requires sub ppm and ppb measurement, these parameters become important for long term stability.

Moreover, the plasma pressure directly affects electron temperature. Our investigations have also shown another source of interference that was not reported in the prior art. Indeed, in various plasma emission cells and generator combinations for analytical applications, the plasma or discharge power is relatively low, generally less than 10 watts. Some generators are coupled to the load (i.e. the discharge cell) inductively, i.e. type H discharge, the other capacitively, i.e. type E discharge. See, for example, "Practical Spectroscopy of High Frequency Discharges", Sergie A. Kazantsev, Vyacheslav I. Khutarshchikov, Gunter H. Guthohrlein, Laurentius Windhoiz, Plenum Press. 1998, ISBN 0-306-45676-1, pp. 7. In such arrangement the excitation signal is AC.

When the power coupling technique is capacitive, the system is generally called a dielectric barrier discharge since there is at least one dielectric barrier between coupling electrodes. In the type H or E system, the field potential is relatively high. Our experiments have shown that, in some cases, the discharge occurs not only in the plasma cell, but some corona discharge can also co-exist at the electrode surrounded by ambient air. The electrodes are normally bounded on the cell wall. The corona discharge occurring on the electrode edge, the emitted light also reaches the photo electric measuring device. This generates spurious variation in the measuring signal. It becomes worse when the relative humidity of ambient air is high. In a system designed to measure low levels of impurities and requiring long term stability, this phenomenon is not acceptable since the generated interference may lead to wrong alarms. The phenomenon was more evident with the capacitive coupling, i.e. type E discharge, since the field potential is higher. With DC or AC direct discharge, the potential is much lower since there is no dielectric. There is DC or AC current flowing between the electrodes. Sometimes the potential could only be about 300 VDC, depending on chamber and electrode design. In this case, there is not enough potential gradients to get corona effect and ionization of the surrounding atmospheric air.

Our investigations have also shown that, for some emission based $N_2$ analyzers used in the field, the inner wall of the cell was coated with a brown color deposit. Such deposit mainly occurred in equipment installed in Air Separation plant truck loading stations. Such deposit was removed from the emission cell, and analyzes revealed that this deposit was mainly composed of Carbon that came from the cracking of some organic compound or Hydrocarbon other than $CH_4$, released by the existing sampling system material or the polluted tanker. Here, by sampling system we mean tubing valves, fittings, filters, etc. There still are many existing sites today that use rotary valves for sample stream selection. Many of these valves have different polymer material and various sealing material and lubricant. At some sites, the use of plastic or polymer flexible lines are common. Nylon for example is a source of Hydrocarbon pollution. Valves having some grease or carbon powder to reduce the friction of the seal around the valve stem are also another source of Hydrocarbons. Some organic compounds simply come from the finger prints left on some parts of the sampling system during its assembly. Such interference results in a lost of sensitivity, since the cell slowly becomes opaque to light transmission.

Another source of carbon contamination is the material used to build the analyzer. Stainless steel tubing, depending on operating conditions, could also release some contamination. We found that the plasma chamber used in our laboratory has such deposit after 5 years of use. The source of deposit comes from the material itself or the so-called "wetted parts" of the system. We also found that the material used to make the emission chamber may have some amount of impurities in it. Normally, a very high quality quartz material is used. However, after many years of use and under the plasma, some parts of the wall's chamber do have some deposit, even with plasma maintained with a very high purity gas. This source of contamination is variable, based on material lot, and happens over a relatively long period of time. Generally, we can see this side effect beginning to appear after two to three years.

However, process analyzer should ideally be reliable for a much longer period of time. So, it would be a real benefit to be able to keep the Inner wall of the emission chamber "clean" or deposit free, in order to maintain long term sensitivity thereof.

h) non linearity phenomenon: As previously mentioned all commercially available $N_2$ analyzers on the market do not have any linearity correction means. There is a reason for this. In fact, over a small range of measurement, the signal is quite linear, like shown in FIGS. 3 and 7. However, in these Figures, only the net signal is measured, i.e. $N_2$ emission intensity substracted from the baseline. Measuring only the net $N_2$ emission at 337.1 nm without substracting the baseline will reduce the linearity when the mixture is not binary. For example, looking at FIGS. 5 and 6, it is easy to see that upon addition of moisture, the emission continuum is going up, while the $N_2$ emission is going down. The presence of other impurities will also affect linearity. This phenomenon is also reported in "Spectroscopic analysis of gas mixtures", O. P. Bochkova and E. Y A. Shreyder, Leningrad State University Academic Press, 1965 SF-4101, where ratiometric measurement is recommended to fix this problem. In "Analyse qualitative d'impuretés dans l'hélium par spectroscopic d'émission", A. Ricard et J. Lefebvre, Analysis, 1978 V.6, No. 7, pp. 299 to 305, the non-linearity resulting from the presence of one or multiple impurities is clearly demonstrated.

Since the present invention, as it will be explained later, uses a method that traps impurities except the $N_2$, and also uses a differential signal, i.e. background signal subtracted from $N_2$ emission, one may think that these features will fix the non-linearity problem. This is true, but only for a limited operating range of $N_2$ in the sample. Furthermore, based on noble gas type, the non-linearity behaviour changes a lot.

As described in "Spectroscopic analysis of gas mixtures", O. P. Bochkova and E. Y A. Shreyder, Leningrad State University Academic Press, 1965 SF-4101, and also in several physic's books related to plasma physic, the amount of concentration of excited atoms or molecules depends on the current or plasma power. It also teaches that the species in presence in a plasma are in competition for the available energy. So, in a binary mixture the ionization efficiency is not the same with a small amount of impurities compared to a higher amount.

Figure 16:
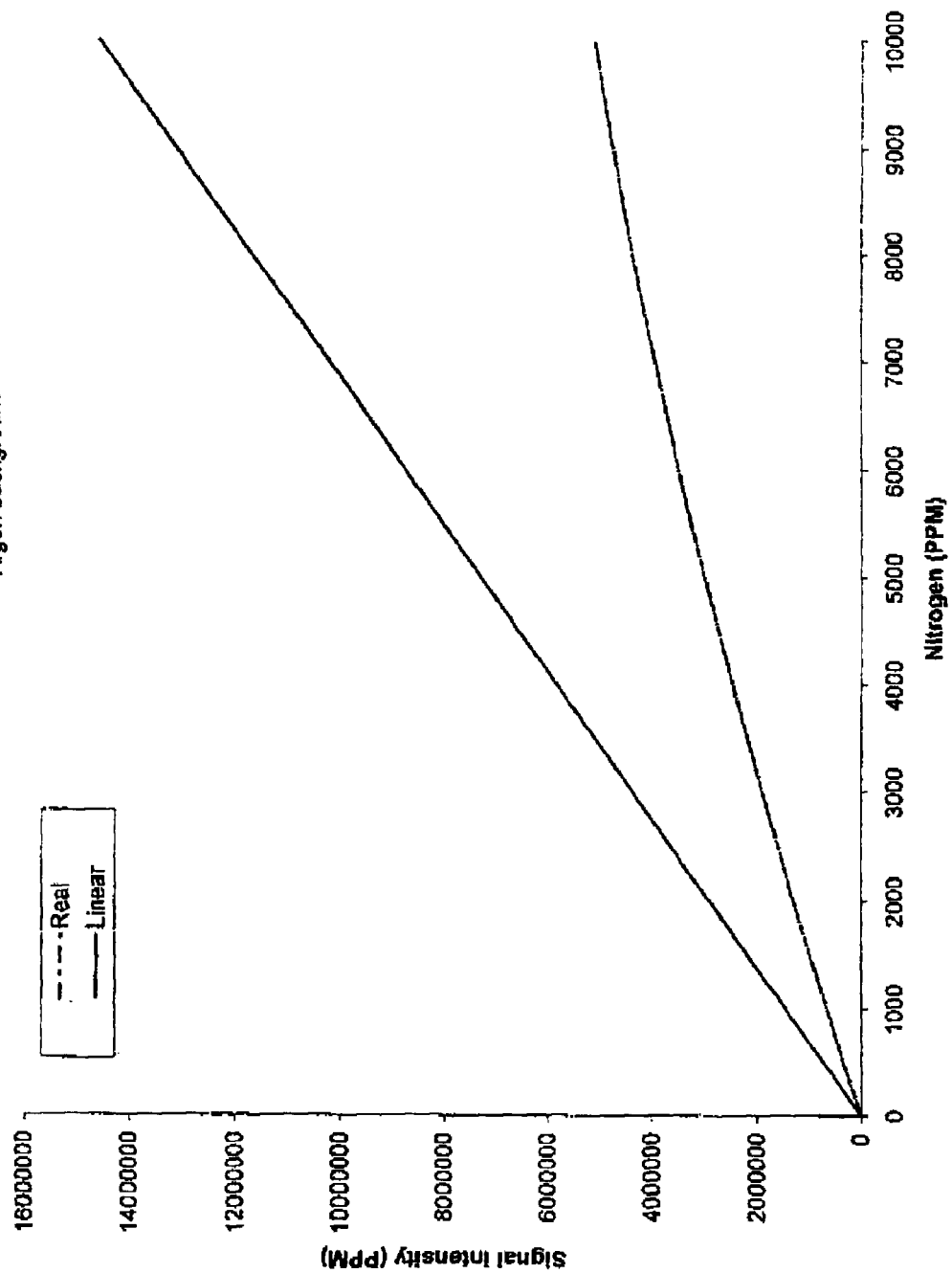
FIG. 16 is a graph of a signal intensity of $N_2$ emission as a function of $N_2$ concentration in Argon (binary mixture).
Figure 17:
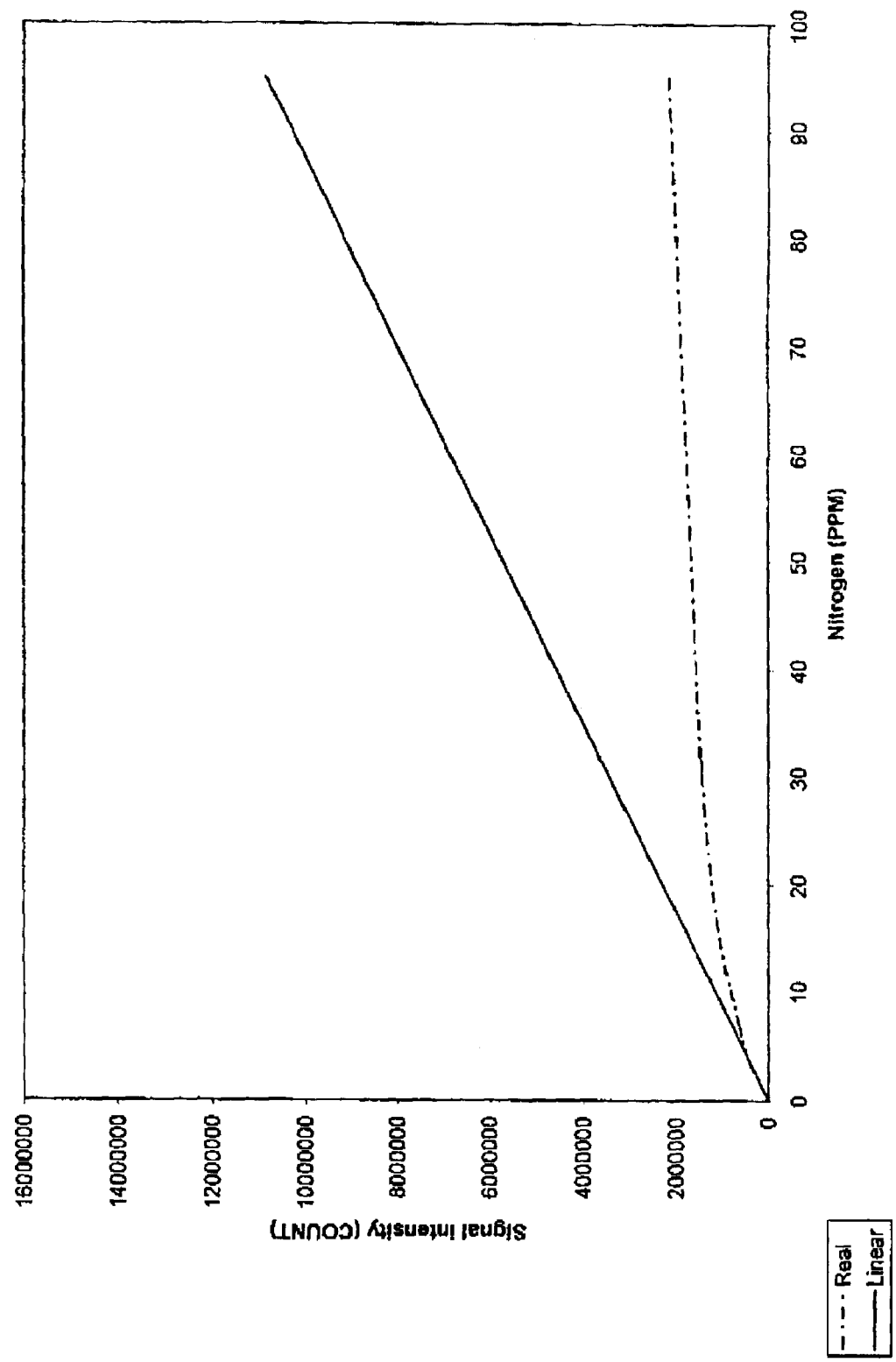
FIG. 17 is a graph of a signal intensity of $N_2$ emission as a function of $N_2$ concentration in Helium background (binary mixture).

FIGS. 16 and 17 respectively show such behaviour for a $N_2$ in Argon and Helium emission system. An increase in $N_2$ level results in a diminution in system sensitivity and then linearity. This is caused by a loss in the energy available from the Argon plasma, due to the $N_2$ population and to phenomenon of ionization of second kind. Here, by the expression "sensitivity", it is meant the increase in signal intensity per unit increase in solute concentration. This shows that even with a binary mixture the non-linearity still is a problem. The situation is even worse with Helium as background. At ppb level of $N_2$ in Helium there is a high sensitivity. When the $N_2$ level is going up, the sensitivity is going down due to quenching.

It would therefore be highly desirable to provide some means to correct linearity issues in order to get a linear reading over a wide range of $N_2$ level, i.e. up to 10,000 ppm.

Prior Art Solutions:

Today, many users have recognized the detrimental effect from other impurities in an Argon sample on the $N_2$ measurement. They also recognized the need to take some action to correct such problems. However, as it will be explained thereinafter, each of the various attempts proposed in the art to cancel interference is always a partial solution.

a) Reference is now made to the following prior art documents: U.S. Pat. Nos. 3,032,554; 5,168,323 and 5,009,099; "Spectroscopic analysis of gas mixtures", O. P. Bochkova and E. Y A. Shreyder, Leningrad State University Academic Press, 1965 SF-4101; "Emission Spectrometric Method and Analyzer for Trace of Nitrogen in Argon". Homer Fay, Paul H. Mohr, and Serard A. Cook, Linde Co. Division of Union Carbide, Analytical Chemistry, Vol. 34, No. 10 Sep. 1962; "Development of an Automated Speciation Analyzer", Bernd Rosenkranz et Al., American Laboratory vol. 31, number 20, October 1999; "A Modular for the Automatic Subtraction of Continuous Background in Optical Spectrometers", Optics and Spectroscopy, February 1964, Vol. 16, No. 2, pp. 184-186, G. M. Svishchev; "A Method of Background Correction for Direct Reading Optical Emission Spectroscopic Analysis Using Offset Exit Slits", Analytical Chemistry vol. 41 No. 2, February 1969, pp. 396-398, John A. Levs, and "A Dynamic Background Correction System for Direct Reading Spectrometry" R. K. Skogerboe et Al., Applied Spectroscopy, vol. 30, No. 5, pp. 495-500, September-October 1976. In these documents, attempts to cancel out the background signal variation effect by subtracting background signal from the impurity emission lines are described. Such correction results in a more stable signal, i.e. less drift. In all these cases, even if the used designs slightly differ from each others, the tests conducted have shown more stable and accurate results by doing background corrections.

However, background correction cannot cancel alone all the detrimental effect: of interference. For example, in the case of spectral interference, background compensation or correction is useless, Furthermore, some physical/chemical effects on a particular emission line of interest, as 337 nm for $N_2$ for example, are not cancelled by background correction. An example of this is the effect of moisture on the $N_2$ emission lines as previously described.

b) Other users have felt the need to reduce the moisture interference on $N_2$ measurement. For example, in "Development of a Detector for Ultratrace Nitrogen in Argon using Low-Pressure Capillary Glow Discharge Molecular Emission Spectrophotometry", Hiroshi Ogino et Al., Anal-Chem. Vol 69, No 17, September 1997, Ogino et Al. use a desiccant to trap moisture from the Argon sample. They use a molecular sieve 5A (60/80 mesh). However, with this embodiment, the $N_2$ molecule will be delayed by passing through this trap since 5A molecular sieve base trap acts like a chromatographic column. Any temperature variation of the trap will cause reading variations. Increasing the trap temperature will release some $N_2$ and vice versa. This will thus cause signal wandering.

Moreover, the use of a desiccant trap will not effectively resolve the interference caused by other impurities like $CH_4$, $O_2$ and $H_2$. In fact, the trap may accentuate the problem. The 5A molecular sieve will also partially trap and delay the passage of $H_2$, $O_2$ and $CH_4$. Flow or temperature variation of the trap will also affect the adsorption behaviour thereof. It results that, when there is flow or temperature variation, $O_2$, $H_2$ and $CH_4$ could be released or adsorbed into the trap. It results in more drift or sudden change on $N_2$ reading.

c) Other users suggest, like in U.S. Pat. No. 5,168,323 previously cited, the use of a computational method to compensate for interference. In the described method, they also take into consideration the signal background. The intensity of various spectral lines of interest is measured. The effective line intensity generated from one particular impurity is computationally determined from linear combinations of the various measured intensities. However, this method has serious drawbacks. First, as it was shown with moisture, the interference effects are not linear. Moreover, it appears that, based on plasma excitation mode and the level of impurities in presence, the various physical/chemical reactions and their rate are not constant. Furthermore, the suggested method does not take into account some parameters that also affect the plasma like the operating pressure and quenching. Quenching occurs when a molecule having been excited to a higher level, is de-excited to a lower level by collision with other molecules before it has spontaneously emitted photons at its characteristic wavelength.

Furthermore, it should also be noted that the background signal does not vary equally in the emission spectrum. Measuring the background emission at only one point for background correction will not work for all impurities because some of them are not subject to the same signal background variation. At the best of our knowledge, the system proposed in the above-mentioned prior art reference was not really commercialized. Another problem of this proposed system resides in the fact that the possibility that the Argon sample can also have CO and $CO_2$ impurities therein is not taken into consideration. It appears that, in theory, by taking into account all the parameters that can affect the $N_2$ emission into the plasma, one can compensate the effect of these parameters on $N_2$ readings. However, in practice, it would require much more than a simple linear combination and it would become really complex and costly to build such system.

d) In U.S. Pat. No. 4,801,209 previously mentioned, Waldow described a method to compensate the interference on $N_2$ measurement caused by the variation of $Ar/O_2$ ratio. The author recognizes the fact that the interference is non-linear and proposes an array of non-linear equations (second order form) with several coefficients that must be determined experimentally by generating various mixtures of $N_2/Ar/O_2$ ratio. It is a long and laborious work that must be repeated for each system built. Another drawback of this compensation or correction method is that only three gases are taken into consideration, i.e. $N_2$, Ar and $O_2$. Furthermore, the proposed method runs correctly for a fairly high amount of $N_2$ in Argon, i.e. from 20 to 2000 ppm. However, for sub ppm measurements, which is the impurity's level that the method of the present invention aims to measure, this prior art method would not be able to provide satisfactory results. Moreover, the method suggested in this patent is for a limited and specific range of sample background, i.e. specific range of Ar and $O_2$ in the background. No other impurities are taken into consideration. The author also reports the effect of atmospheric pressure variation on the system response. However, no compensation means is proposed.

e) In U.S. Pat. No. 5,570,179, Weckstrom described a method wherein there can be a computational base system to correct the effect of $CO_2$ and $O_2$ and some other gases on $N_2$ measurement. Separate sensors like infrared for $CO_2$ measurement, paramagnetic for $O_2$ measurement and other gas sensors are connected to a microprocessor system. In this method, no equation or relationship is reported. The manufacturing of such system would be complex and expensive for a limited performance.

f) In U.S. Pat. No. 4,898,465, Crawford et Al. use a cold cathode gas discharge excited with DC current as emission cell. They report interference on $N_2$ caused by $O_2$ and $CO_2$. They also report signal variation caused by system pressure. They suggest the use of a control loop to adjust the power or the current of the discharge based on species to be analyzed. However, this method would become impractical with multiple impurities in the sample. There is no way to know which species are responsible for signal variation.

After all the efforts done by various workers in the attempt of resolving interference problems on $N_2$ measurement, there still are unresolved interference problems. As previously mentioned, the use of a trap for moisture doesn't resolve the problem caused by $H_2$, $O_2$ and $CH_4$. Moreover, the use of computational model becomes extremely complex and laborious so only partial solutions were described.

Paradoxically, it should be mentioned that, in U.S. Pat. Nos. 5,412,467; 5,831,728 and 6,043,881, no interference at all were reported. The same type of discharge that was used by many other workers listed above was however used.

In U.S. Pat. Nos. 5,412,467 and 5,831,728, the authors state that measurement of $N_2$, $H_2O$ and $CH_4$ could be done in the same spectroscopic cell and that the impurities do not interfere with each other. However, the tests we conducted and all other prior art references we described thereinabove provide different results. As far as we know, such multi-impurities systems with parallel measurement of these impurities were not really commercialized. Moreover, in these references, no data is really available. This leads to believe that few parameters in their experiment have been neglected. In U.S. Pat. No. 6,043,881, the use of emission cells serially connected is suggested. This configuration is suggested for multi impurity measurements including $N_2$. The measurement of $H_2O$, $CH_4$ and $N_2$ is also suggested, even at sub ppm levels. However, due to the nature of plasma discharge, the impurity level in the second cell will not be the same as in the first one. This is due to various chemical reactions occurring with various impurities. So, the first emission cell modifies the nature of the sample flowing into the second cell. Our experiments have shown that the levels of $N_2$ are not the same in both cells. This was easily tested by turning OFF and ON the plasma in the first cell. $N_2$ reading was going down while the plasma was ON in the first cell.

Actually, in all commercially available instruments that measure $N_2$ in Ar and He, they use dielectric barrier discharge at atmospheric pressure. It makes sense to use these systems since the emission spectrum is almost the same as more complex systems based on microwave, radio frequency or running with vacuum pump. However, at the best of our knowledge, none of them use means to compensate or cancel out the interference caused by other impurities in the sample, or simply caused by the ambient operating condition. Nevertheless, these systems are performing relatively well in the case of a binary mixture, but the signal is not linear.

Thus, as already mentioned above, it would be a real benefit to provide an improved method and an improved system to do the measurement of $N_2$ in rare gases using emission spectroscopy that will have a high sensitivity without the interference and linearity problems cited above.

Present Invention:

Accordingly, the present invention proposes a method for on line measurement of $N_2$ in noble and rare gases based on emission spectroscopy which provides very stable, sensitive and interference free results.

In brief, the method must eliminate the following interferences on $N_2$ measurement:

Interference from other impurities; physical/chemical or spectral interference caused by the presence of $H_2O$, $O_2$, $CH_4$, CO, $CO_2$, $H_2$ and organic compound of heavier Hydrocarbons from sampling system. Table 1 below shows the effect of some impurities on the $N_2$ measurements. These are the most common impurities that could be found in the field.

TABLE 1

Molecular band observed in a plasma discharge in presence of $N_2$ and $H_2O$, $H_2$, $CH_4$, $O_2$.

| SPECIES | WAVE-LENGHT (nm) | IMPURITY | INTERFERENCE TYPE | EFFECT ON $N_2$ READING |
|---|---|---|---|---|
| $N_2$ | 337.13 357.69 375.54 380.49 | NONE | NONE | |
| NH | 336.01 337.0 | $CH_4$ or $H_2$ | PHYSICAL/ CHEMICAL SPECTRAL | HIGHER READING |

TABLE 1-continued

Molecular band observed in a plasma discharge in presence of $N_2$ and $H_2O$, $H_2$, $CH_4$, $O_2$.

| SPECIES | WAVE-LENGHT (nm) | IMPURITY | INTERFERENCE TYPE | EFFECT ON $N_2$ READING |
|---|---|---|---|---|
| CN | 388.34 387.14 386.19 | $CH_4$ | PHYSICAL/ CHEMICAL | |
| CH | 431.42 | $CH_4$ | PHYSICAL/ CHEMICAL SPECTRAL | |
| OH | 302.12 306.36 306.72 307 308.9 | $H_2O$ | PHYSICAL/ CHEMICAL | LOWER READING |
| NO | 200-300 | $O_2$ | PHYSICAL/ CHEMICAL | LOWER READING |

Interference from ambient operating conditions: i.e. plasma operating pressure variation caused by atmospheric pressure change and any exterior emission caused by ionization occurring outside the cell in the surrounding atmosphere.

problems inherent to plasma physic resulting in non-linearity; and problems related to change in transmittivity of the cell wall mainly due to carbon deposit over the time from various sources.

Based on our investigations and the available prior art, it appears that it is very difficult and complex to cancel out the influence of typical impurities found in noble gases on the $N_2$ measurement.

The concept of the method of the present invention is based on a combination of means instead of relying only on computational methods, baseline correction or trapping impurities alone.

Therefore, the method according to the invention, also called method of eliminating interference for impurities measurement in noble gases, comprises the steps of:

a) providing a gas sample having interfering impurities and an impurity to be measured therein;

b) providing a plurality of trapping means serially connected to define an impurities trap having an inlet and an outlet, each of the trapping means being adapted to trap a specific one of the interfering impurities without affecting the impurity to be measured;

c) introducing the gas sample at the inlet of the impurities trap for removing the interfering impurities;

d) adding moisture to the gas sample at the outlet of the impurities trap;

e) introducing the gas sample in a plasma cell of a plasma emission system;

f) collecting an emission light generated by the plasma cell at a specific emission wavelength not subjected to spectral interference for providing an emission signal representative of a concentration of the impurity to be measured of the gas sample; and g) measuring the concentration of the impurity to be measured according to the emission signal provided in step f).

Our observations reveal that there is interference coming from: $H_2$, $O_2$, $CH_4$, CO, $CO_2$, NMHC, organic compound and $H_2O$. In the worst case, each of these impurities may be present in the sample at the same time than $N_2$ to be measured. Our investigations have shown that most of these impurities could be trapped with a specially designed multi-layer trap.

This trap has to be specially designed to avoid any interference with the $N_2$ impurities. Thus, according to the concept of the method of the present invention, each of the impurities will be considered one by one. It should be mentioned that the material used in various trap layers must not affect the $N_2$ impurity to be measured.

Generally, the method proposed in the present invention partially relies on trapping the unwanted impurities. According to this concept, a multi-stage or layer (also called bed) of specific trapping material will be described hereinafter. The hereinbelow described system has been tested and has provided good results. However, ft is important to note that other trapping technologies could be envisaged as long as they do not affect the $N_2$ impurities. So, it is to be understood that the following description is not limitative and is given as an exemplary embodiment only.

The first impurity to be removed is $H_2O$. For this purpose, a molecular sieve with a pore diameter less than 4 Å angstroms is advantageously selected. In fact, our investigations have shown that the best results were obtained with 3A molecular sieves. The 3A sieves do not retain the $N_2$ molecule, it just goes through. However, like previously mentioned, the effects of $H_2O$ on $N_2$ intensity and background emission are more apparent when there is a slight change from dry sample to few ppm (about 2) of moisture. Even if our 3A based trap is efficient to remove $H_2O$ without affecting $N_2$ in the sample, a slight change in its operating condition leads to a change in $H_2O$ adsorption. It results that there could be a small change of $H_2O$ at the outlet due to a change in operating condition, which would lead to some interference on $N_2$. Paradoxically, even if this change in $H_2O$ level is small, it happens in the range wherein the $H_2O$ effect has a more apparent impact on $N_2$ and background signal. Thus, to resolve this issue, some water is advantageously added to the dehydrated Argon sample. This way, the plasma operating point is biased in terms of water level. The quantity of $H_2O$ added is high enough to set the operating point where a small change of $H_2O$ level at the outlet of the $H_2O$ trap, does not affect at all the $N_2$ reading. The added level of $H_2O$ is called the saturation point. Here, when this saturation point is reached, there is no more effect on $N_2$ emission when there is a slight change in $H_2O$ level. The interference caused by $H_2O$ in the sample was thus completely eliminated, without affecting the $N_2$ impurities.

The second impurity to consider is Oxygen. Oxygen is easily and advantageously trapped by a reduced Copper based catalyst. Here again, the trapping material must not affect the $N_2$ impurities. Most Copper based catalysts are based on Copper finely dispersed on a support. The support is designed for an increase surface area to maximise the contact with the flowing gases. The idea is to select a Copper based catalyst having a pore diameter that will have little effect on $N_2$ while trapping the $O_2$ impurities. Furthermore, it should be mentioned that it can be advantageous to heat the Copper catalyst at some point, since it increases its capacity to trap $O_2$ and speeds up the passage of $N_2$ there through. This point is relatively important when the sample is Helium since Helium has a much lower molecular weight than $N_2$. Thus, increasing trap temperature has a real benefit on $N_2$ impurities in the sense that $N_2$ has much less tendency to be delayed by the supporting material of the catalyst. This has efficiently resolved the problems caused by the $O_2$ impurities on $N_2$ measurement. A suitable catalyst which can advantageously be used is the R3-11, R3-12 or R3-15 from BASF Company. However, it is worth mentioning that other suitable catalysts could also be envisaged.

For Hydrogen Impurities, a catalyst having high affinity for $H_2$ is selected. In this case, a Palladium based catalyst is advantageously chosen. Here again, the catalyst support material should leave the $N_2$ impurities unaffected. This is done by selecting the proper pore size and operating temperature like done for the $O_2$ impurities. Palladium has a very high adsorption capacity for $H_2$. It could adsorb up to 900 times its own $H_2$ volume. With this specific catalyst the $H_2$ impurities are efficiently removes from the sample while the $N_2$ are leaved unaffected.

Now, concerning CO, $CO_2$ and NMHC impurities, such impurities are advantageously effectively removed from the sample by a Nickel based catalyst, like reported in U.S. Pat. No. 4,713,224. Here, special care has to be taken to avoid affecting the $N_2$ passage through this catalyst. Our experiments have shown that, by adjusting the mesh size of the catalyst, impurities were still effectively removed while $N_2$ impurities remained unaffected. Again, operating temperature should preferably be constant. It should be noted that a Nickel catalyst is also able to sorb $H_2$. A Palladium based catalyst for trapping $H_2$ is however preferred. In fact, Nickel catalyst will effectively remove from the sample the $H_2O$, $O_2$, CO, $CO_2$, $H_2$ and NMHC impurities. It will also reduce $CH_4$ content. However, as previously mentioned, in the present invention, the use of more specific catalysts for individual impurity removal is preferred. Thus, this way, it is easier to estimate the system performance based on catalyst manufacturer data.

With respect to the organic compounds, the method of the present invention advantageously relies on a trap based on an activated carbon. Activated Carbon has been used for many years to remove impurities from different types of liquid or gas fluids. Based on the activation method and the raw material used, the activated carbon could be made more specific to some impurities. The use of layers of proper activated carbon will advantageously efficiently remove NMHC, organic compound and will also contribute to reduce the level of $CH_4$. The choice is governed by the effect of this layer on $N_2$ impurities. Our experiments have shown that a deeply dehydrated coconut charcoal type activated carbon gives excellent results even if other arrangements could be considered. It should however be noted that the carbon bed temperature must preferably be kept constant.

Figure 11:
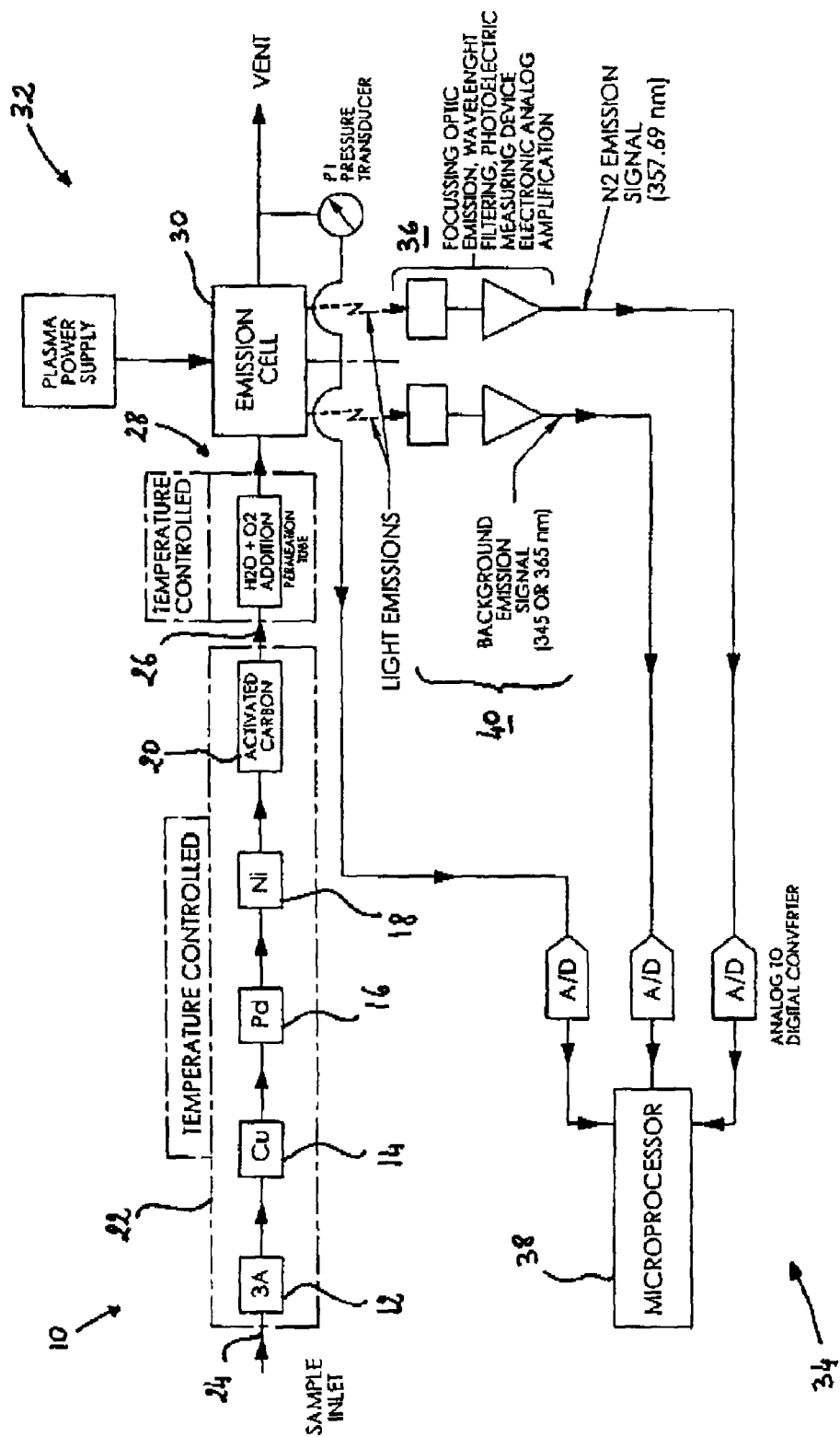
FIG. 11 shows a functional block diagram of a plasma emission base system, according to the present invention.

Referring now to FIG. 11, there is shown a functional block diagram of a preferred embodiment of the system the present invention, also called a system of eliminating interference for impurities measurement in a gas sample having interfering impurities and an impurity to be measured therein. The system 10 is provided with a plurality of trapping means 12, 14, 16, 18, 20 serially connected to define an impurities trap 22 having an inlet 24 and an outlet 26. Each of the trapping means 12, 14, 16, 18, 20 are adapted to trap a specific one of the interfering impurities without affecting the impurity to be measured. Preferably, as previously mentioned, the plurality of trapping means advantageously comprises a molecular sieve 12 for trapping $H_2O$ impurities, a reduced copper based catalyst 14 for trapping oxygen impurities, a palladium based catalyst 16 for trapping hydrogen impurities, a nickel based catalyst 18 for trapping CO, $CO_2$ and non-methane hydrocarbon impurities, and an activated carbon based catalyst 20 for trapping organic compounds.

The system 10 also has means 28 for adding moisture to the gas sample. These means 28 are serially connected to the outlet 26 of the impurities trap 22. The system 10 is also provided with a plasma cell 30 of a plasma emission system 32 serially connected to the means 28 for adding moisture for generating an emission light representative of a concentration of the impurity to be measured of the gas sample. The system 10 also has processing means 34 operatively connected to the emission cell 30 for processing the emission light and providing the concentration of the impurity to be measured. Preferably, the processing means 34 is provided with collecting means 36 for collecting the emission light at a specific emission wavelength not subjected to spectral interference, preferably 357.69 nm for $N_2$ measurements, to provide an emission signal representative of a concentration of the impurity to be measured. The processing means 34 further has a microprocessor 38 for processing the emission signal and providing the concentration of the impurity to be measured.

As illustrated, once assembled, properly activated and conditioned, each of these above-described traps are then serially connected. Each of these traps is advantageously kept at constant temperature and the sample flow is also preferably kept constant, thanks to flow control means (not shown). This is relatively important since, if sample flow varies, the addition of $H_2O$ will also change. The $H_2O$ is preferably added with a permeation tube device. Since the permeation rate is constant under controlled ambient conditions, a flow variation will change the dilution factor through the tube.

When the sample gas comes out of the last trapping means 20, there is only $N_2$ and very little $CH_4$, if any. Then, water or moisture is added to the gas sample in order to minimize the effect of slight change of its level on the $N_2$ emission like previously mentioned. This cancels out the detrimental effect of moisture on $N_2$ measurement since all impurities, i.e. $H_2O$, $O_2$, $H_2$, CO, $CO_2$, NMHC and some other organic compounds are trapped. There is only the $CH_4$ who can still cause problems because it is not trapped at 100%. $CH_4$, as previously mentioned, results in spectral interference on $N_2$ emission at 337.1 nm. For this reason, the 357.69 nm $N_2$ emission line is advantageously selected. As illustrated in FIG. 10, this emission line is not affected by any spectral interference from NH emission at 336 and 337 nm.

However, there could be a slight change in background emission caused by $CH_4$. To eliminate this source of interference only caused by $CH_4$ (the other impurities are trapped and water level is constant because of the controlled permeation rate of the $H_2O$ addition module), the baseline or background emission is advantageously measured in the neighbourhood of the 357.69 nm $N_2$ emission. This background emission is then subtracted from the $N_2$ (357.69 nm) emission by the processing means. This way, the background variation interference on the $N_2$ (357.69 nm) is advantageously cancelled. Background measurements at 345 nm and 365 nm have also been tested and work well. Thus, in order to implement the above-described background subtraction, the processing means 34 is advantageously further provided with background collecting means 40 for collecting a background emission light generated by the plasma cell 30 at an emission wavelength neighbouring the specific emission wavelength to provide a background emission signal. The microprocessor 38 is adapted for subtracting the background emission signal from the emission signal to provide a net emission signal representative of the net emission of the impurity to be measured, thereby cancelling background variations.

The permeation tube, which is advantageously used for the addition of $H_2O$ is preferably a sample Teflon™ tubing surrounded by water. The temperature of the tube is advantageously kept constant, so its permeation rate. In such configuration, a gas phase space must be kept to avoid mechanical failure due to pressure build up. By filling the void space with pure $O_2$ or a mix of $O_2$ and sample background and adjusting the length of permeation membrane, an amount Of $O_2$ will also be added to the sample gas. This small amount of $O_2$ into the plasma will react with any carbon deposit by "etching" it. It results that the cell wall stays clean even if Hydrocarbons are voluntarily added at the cell inlet. This solution is effective and economic to keep the plasma cell clean over an extended period of use. A separate permeation tube for oxygen addition could also be used for $O_2$ addition.

Now, still referring to FIG. 11, since the plasma is operated at atmospheric pressure, atmospheric pressure variation will cause variation in emission intensity. To resolve this issue an atmospheric pressure transducer P1, or any other suitable measuring means, is advantageously used to measure the plasma cell discharge pressure. This signal is then used by the microprocessor 38 to compensate the effect of pressure on the $N_2$ signal and on background signal. Then, to eliminate interference from emission outside the emission chamber 30, the system is advantageously provided with an insulating enclosure (not shown) for insulating the plasma chamber 30 from surrounding. Preferably, this chamber 30 is advantageously sealed by proper potting material. Alternatively, only glass deposition on the external face of the electrode may be preferred.

Our experiments have shown that this solution is very effective to eliminate ionization of surrounding atmosphere even with relatively high field potential.

As previously described, the last problem to be solved is the linearity. As shown in "Spectroscopic analysis of gas mixtures", O. P. Bochkova and E. Y A. Shreyder, Leningrad State University Academic Press, 1965 SF-4101, and in "Analyse qualitative d'impuretés dans l'hélium par spectroscopic d'émission", A. Ricard et J. Lefebvre, Analysis, 1978 V.6, No. 7, pp. 299 to 305, dependent on operating conditions, the $N_2$ measurement in rare gas is not linear. The measurement of $N_2$ in He seems to be the worst case, mainly at low levels. In Argon, the problem arises at high levels of $N_2$. To correct such non-linearity, a computational method or a correcting algorithm embedded in the microprocessor 30 could advantageously be used. The linearization method consists in recording the system signal in function of Nitrogen levels, then a polynomial curve fitting equation could advantageously be used. A simple look up table with a linear evaluation between each point could also be implemented. Such software routine is advantageously built into the microprocessor.

Such software method is performing well but does not resolve the loss of sensitivity when $N_2$ level is increasing. Here we mean by the expression sensitivity the increase in signal intensity per unit of increase in solute concentration.

According to this, another correcting means could be applied in order to achieve linearity and constant sensitivity over a wide range of operation. In such configuration an instrument could advantageously be re-ranged to still provide sub ppb sensitivity.

Figure 18:
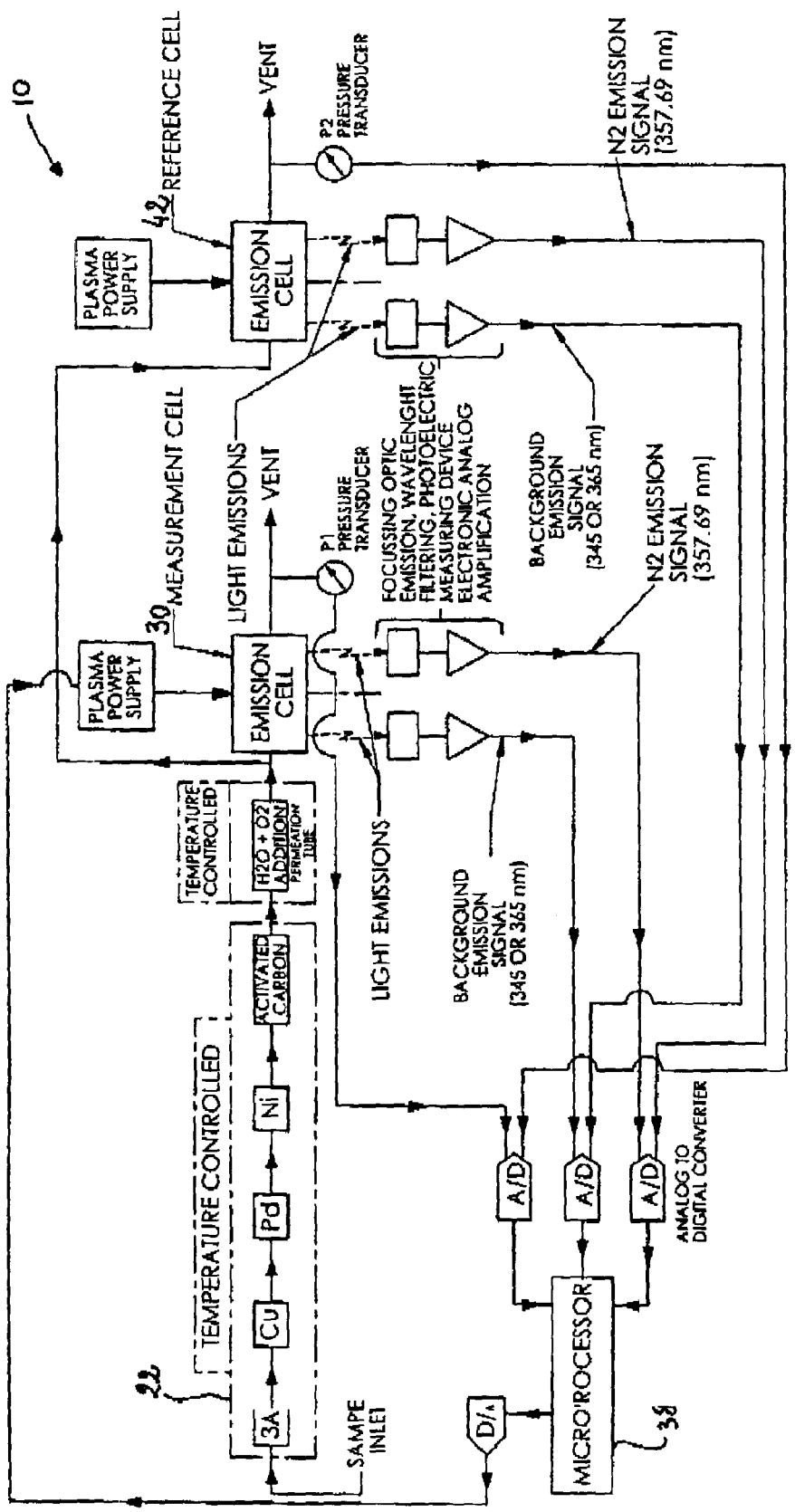
FIG. 18 shows a functional block diagram of a plasma emission base system according to the present invention wherein a reference cell has been added for non-linearity compensation.

The system illustrated in FIG. 18 shows such a configuration. In this configuration, a second plasma cell 42, also called reference plasma cell, and associated generator are advantageously used. This reference cell 42 is connected in parallel with the emission cell 30 and the sample gas is split between both plasma cells 30, 42. This reference plasma cell 42 allows to generate a reference emission light representative of a concentration of the impurity to be measured. In other words, this cell gives the $N_2$ level to the microprocessor 38.

Based on the level of $N_2$, the microprocessor 38 readjusts the plasma power of the measurement cell 30, thereby compensating for the non-linearity. So, the $N_2$ measurement signal coming from the measurement cell is a straight line from 0.25 ppb up to 10,000 ppm. The frequency of the plasma could also be changed to increase the emission rate of $N_2$.

Figure 12:
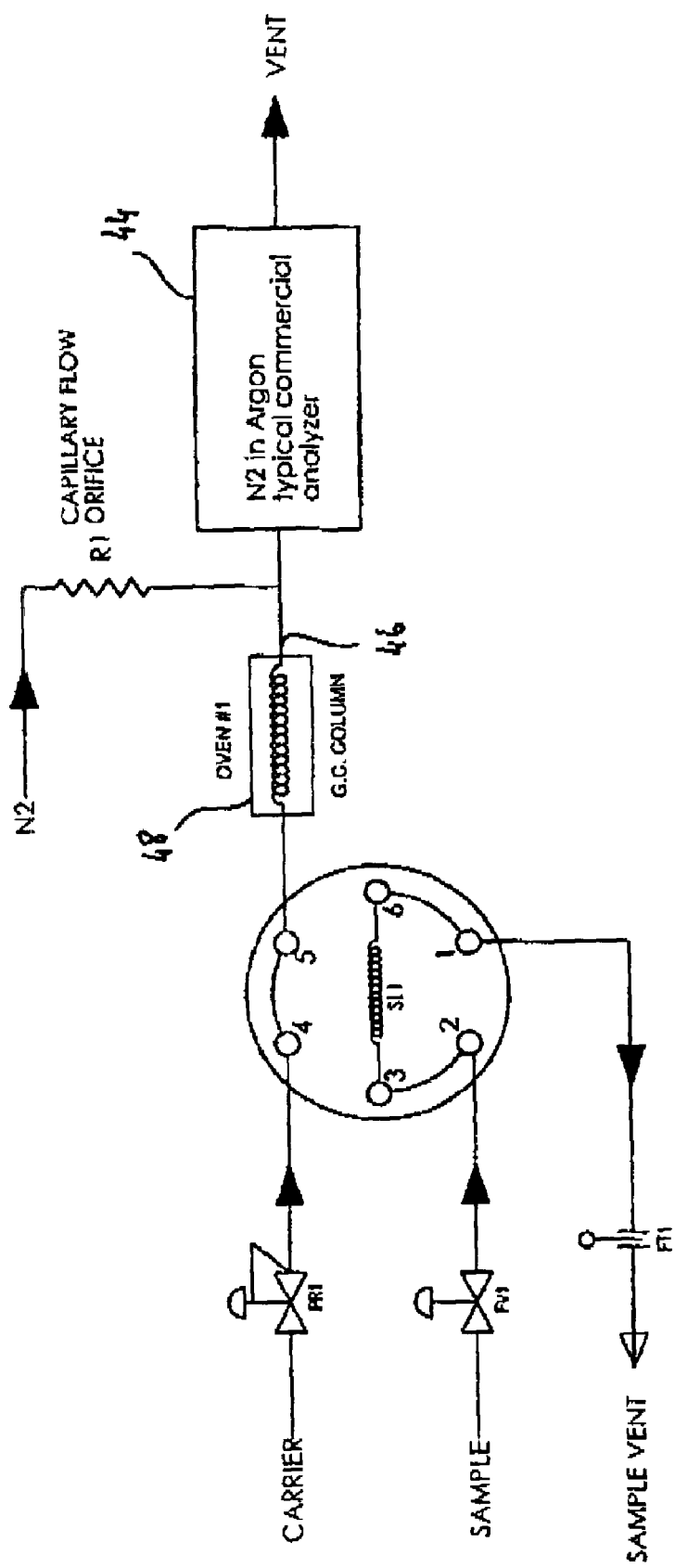
FIG. 12 shows a functional block diagram of an interference testing setup, according to the present invention.
Figure 13:
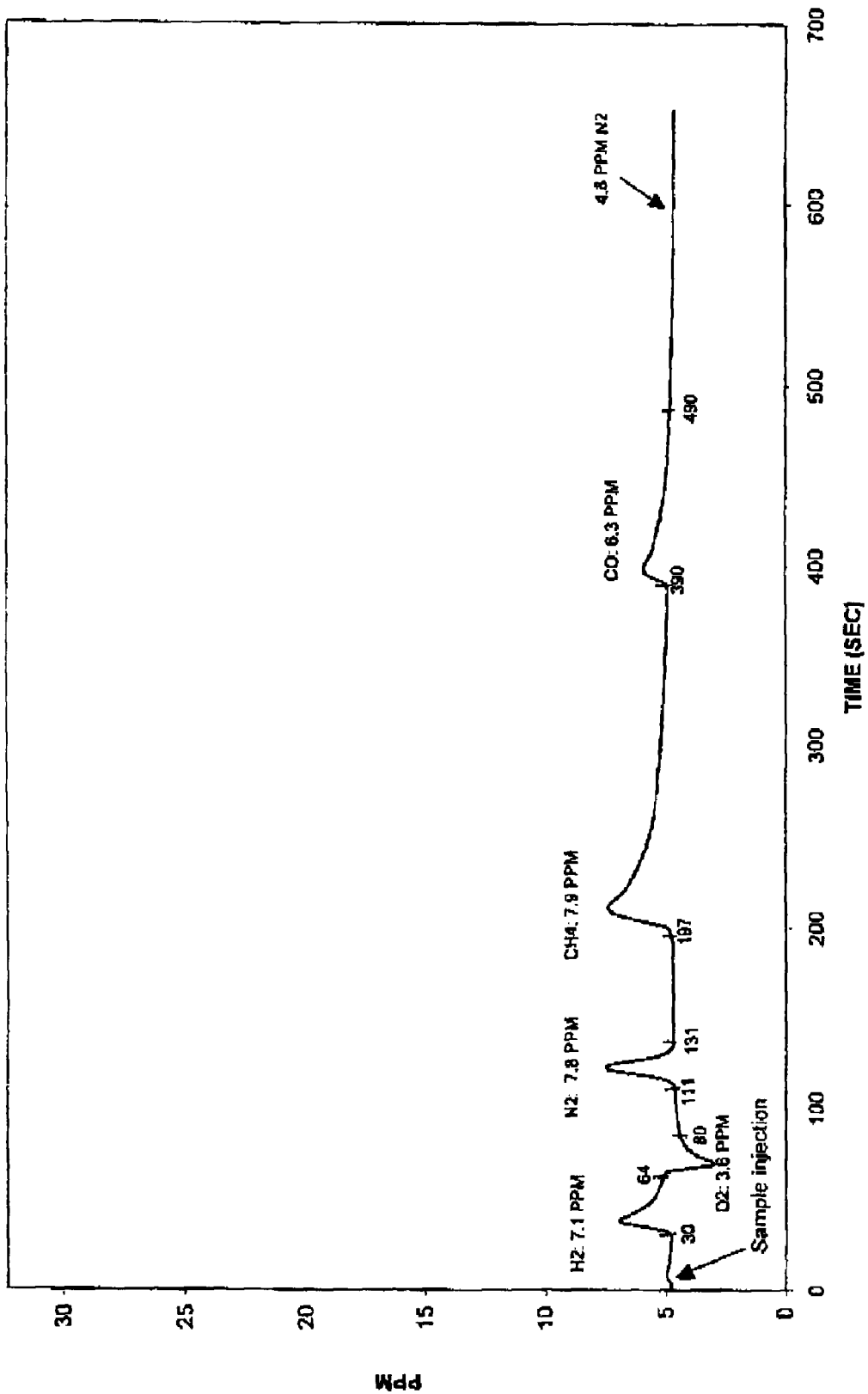
FIG. 13 (PRIOR ART) is a graph illustrating the typical system performance of a typical system known in the art.
Figure 14:
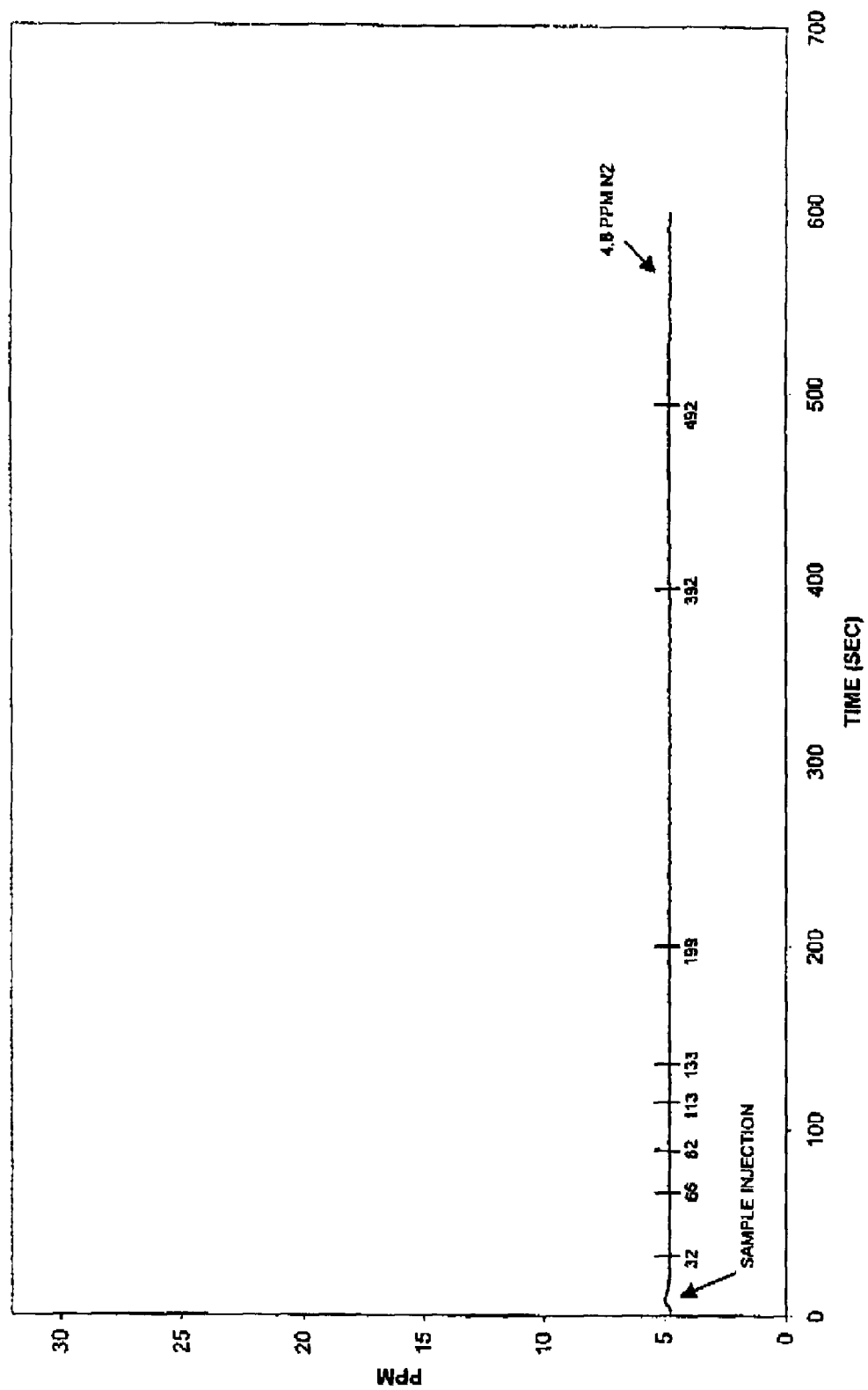
FIG. 14 is a graph illustrating the system performance of the system of the present invention.
Figure 15:
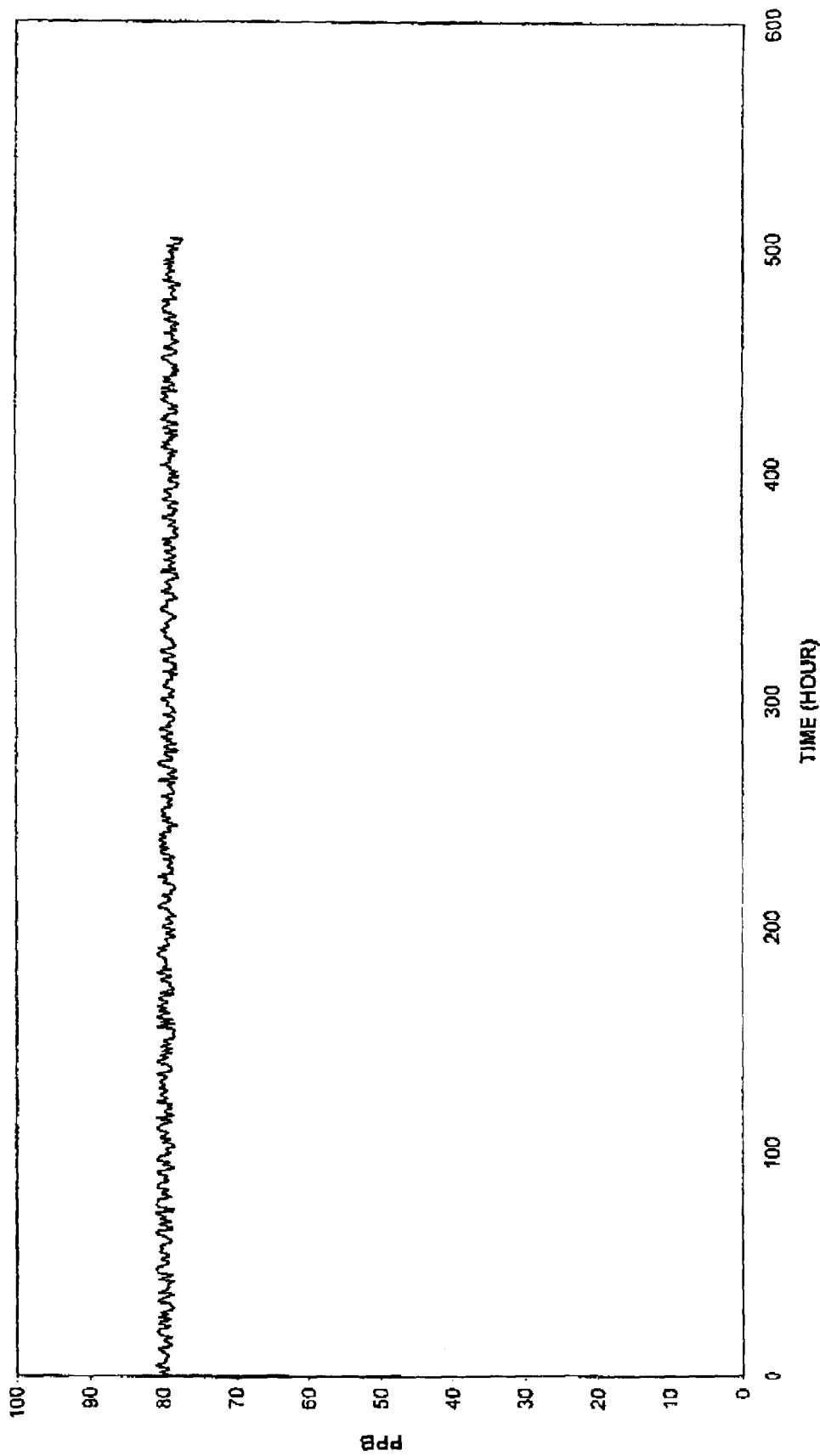
FIG. 15 is a graph illustrating the long term stability of the system of the present invention.

With reference to FIGS. 13 to 15, the performance of the system of the present invention will now be analysed. Firstly, a typical system performance in regards to other impurities in the sample is shown in FIG. 13. This performance test was done with the interference testing setup shown in FIG. 12. In the illustrated setup, a typical $N_2$ in Argon analyser 44 using a dielectric barrier discharge is connected to the outlet 46 of a chromatographic column 48. The column 48 is swept by a pure Argon carrier gas. The $N_2$ in Argon analyzer 44 was calibrated with the pure Argon carrier gas for the zero point and a reference of 10 ppm $N_2$ in Argon for the span. This is a typical $N_2$ analyzer calibration value used in the Air Separation Industries. Now, $N_2$ is added at the inlet of the $N_2$ analyzer through the dilution orifice R1. This $N_2$ flow is adjusted to get a reading around 5 ppm on the $N_2$ analyzer display. The interference testing setup is also provided with a sample loop SL1. A gas sample flows through SL1. This gas sample is a mixture of $H_2$, $O_2$, $N_2$, $CH_4$ and CO in Argon. Each impurity is ranging from 2 to 3.5 ppm. The idea is to inject the SL1 volume into the molecular sieve 5A G.C. column 48. Then each impurity will come out of the G.C. column 48 in the following order: $H_2$, $O_2$, $N_2$, $CH_4$ and CO. By monitoring the analyzer reading, the effect of each of these impurities on $N_2$ reading could be evaluated. The result is shown in FIG. 13. FIG. 14 shows an emission $N_2$ analyzer signal, but with the method of the present invention. The same sample as previously described is injected. As it can be seen in FIG. 14, there is no signal variation detected.

It is also important to mention that long term stability is a major issue with on line measurement systems. FIG. 15 shows signal stability of a $N_2$ analyzer built according to the method of the present invention. As illustrated, the system drift was less than 1 ppb with noise less than 0.25 ppb. This was for a $N_2$ in Argon system. These performances were not achieved until now. We extended the drift test period over 3 weeks, and we got a maximum deviation of 1.5 ppb. Many factors could have generated this deviation. Noise stays at maximum of 0.25 ppb. These results outclass any commercial $N_2$ analyzer available on the market. The above-described drift test was performed with a system built according to the method of the present invention and calibrated with 80 ppb $N_2$ in Argon.

It should be mentioned that, in a preferred embodiment of the present invention, each trapping means is respectively particularly designed to trap 5 ppm of each gas continuously for a period of one year. It takes a few grams of each different material except for the molecular sieve 3A and the copper based catalyst where we used a much larger quantity in case of atmospheric contamination. Of course, for a particular application, one can envisage other configurations.

In conclusion and according to the experiments that were performed, the on line measurement of $N_2$ in noble gases based on emission spectroscopy using the method of the present invention results in interference free, extremely stable, low noise and linear measures. The proposed method relies on a combination of a plurality of means that are particularly arranged together to correct linearity issues and to cancel interference. According to the best mode of the invention, this combination of means advantageously comprises:

1) Trapping the impurities that interfere with the $N_2$ measurement without affecting the $N_2$ impurities.

2) Selecting an emission wavelength that is not subject to spectral interference from NH emission at 336 and 337 nm, i.e. 357.69 nm. It should however be noted that other $N_2$ emission wavelengths could also be used if all impurities are completely eliminated with the trapping means.

3) Adding moisture to the sample gas just before the plasma chamber in order to stabilize the effect of a slight moisture variation. Indeed, a slight moisture variation in a dry sample results in stronger interference compared to the same variation on a "moisturized" sample.

4) Cancelling the background variation by measuring the background signal in the neighbourhood of the $N_2$ emission wavelength used and subtracting this background signal off the $N_2$ emission wavelength. So the net $N_2$ emission is advantageously used.

5) Measuring plasma pressure and compensate the $N_2$ emission based on the measured pressure.

6) Ensuring that surrounding cell atmosphere will not become ionized. This can be done by sealing the electrode or by enclosing the plasma cell in proper potting compound, thereby eliminating all air surrounding the system.

7) Adding a small amount of $O_2$ to the sample gas at the inlet of the plasma emission system, to eliminate carbon deposit inside the plasma cell in order to keep it clean and avoid lost of sensitivity over the time.

8) Compensating signal non-linearity through a simple software algorithm or by adjusting measurement cell plasma power based on $N_2$ level. Plasma power or frequency could advantageously be controlled to do so.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention. For example, the method of the present invention has been described for $N_2$ in Argon. It is however worth mentioning that the present invention could also be applied to $N_2$ in Helium, Neon or Krypton, and could even be applied to other impurities measurements.

What is claimed is:

1. A method for impurities measurement in noble gases, comprising steps of:
    a) providing a gas sample having at least one interfering impurity and at least one impurity to be measured therein, wherein at least one impurity to be measured is an impurity other than $H_2O$;
    b) providing at least one trapping means to define an impurities trap having an inlet and an outlet, said at least one trapping means being adapted to trap at least one interfering impurity without affecting the at least one impurity to be measured;
    c) introducing the gas sample at the inlet of the impurities trap for removing said at least one interfering impurity;
    d) reducing the effect of variations in moisture content within the gas sample on measurement of a first impurity to be measured, wherein said first impurity is an impurity other than $H_2O$, by adding moisture to the gas sample;
    e) introducing the moisturized gas sample obtained in step (d) in a plasma cell of a plasma emission system;
    f) collecting an emission light generated by the plasma cell at a specific emission wavelength not subjected to spectral interference for providing an emission signal representative of a concentration within the sample gas of at least said first impurity to be measured; and
    g) measuring the concentration of at least said first impurity to be measured according to the emission signal provided in step (f).

2. The method for impurities measurement in noble gases according to claim 1, wherein the gas sample comprises argon and the first impurity to be measured comprises nitrogen.

3. The method for impurities measurement in noble gases according to claim 2, wherein, in said step f), the specific emission wavelength is 357.69 nm.

4. The method for impurities measurement in noble gases according to claim 1, further comprising a step of controlling a temperature of the impurities trap to maintain a constant temperature thereof.

5. The method for impurities measurement in noble gases according to claim 1, wherein in said step d), said moisture is added with temperature controlled means.

6. The method for impurities measurement in noble gases according to claim 1, further comprising a step of maintaining constant a flow of the gas sample during said steps d) to e).

7. The method for impurities measurement in noble gases according to claim 1, wherein said at least one trapping means is adapted to trap at least one of $H_2O$, $O_2$, $CH_4$, $CO$, $CO_2$, $H_2$, organic compounds and non-methane hydrocarbon impurities.

8. The method for impurities measurement in noble gases according to claim 1, further comprising a step of isolating the plasma cell from surroundings.

9. The method for impurities measurement in noble gases according to claim 1, further comprising, before step g), steps of:
collecting a background emission light generated by the plasma cell at an emission wavelength neighbouring the specific emission wavelength for providing a background emission signal; and
subtracting the background emission signal from the emission signal to provide a net emission signal representative of the net emission of the impurities to be measured, thereby cancelling background variations.

10. The method for impurities measurement in noble gases according to claim 1, further comprising steps of:
measuring a plasma pressure of the plasma cell; and
compensating the emission signal representative of the concentration of the impurity to be measured according to the plasma pressure.

11. The method for impurities measurement in noble gases according to claim 1, further comprising a step of compensating a non-linearity of the emission signal.

12. The method for impurities measurement in noble gases according to claim 11, wherein the step of compensating comprises a step of adjusting a driving power of the plasma cell according to the concentration of the impurity to be measured.

13. The method for impurities measurement in noble gases according to claim 11, wherein the step of compensating comprises a step of applying a correcting algorithm dependent on the concentration of the impurity to be measured.

14. The method for impurities measurement in noble gases according to claim 1, further comprising steps of:
providing a reference plasma cell connected in parallel with the emission cell for generating a reference emission light representative of a concentration of at least one impurity to be measured;
processing said reference emission light for providing a level of the concentration of the at least one impurity to be measured; and
adjusting a driving power of the plasma cell according to the level of the concentration of the at least one impurity to be measured.

15. The method for impurities measurement in noble gases according to claim 1, wherein the step of adding moisture to the gas sample comprises adding moisture at the outlet of the impurities trap.

16. The method for impurities measurement in noble gases according to claim 1, wherein the step of adding moisture to the gas sample comprises a controlled addition of moisture to achieve a constant moisture level.

17. A system for impurities measurement in a gas sample having at least one interfering impurity and at least one impurity to be measured therein, wherein at least one impurity to be measured is an impurity other than $H_2O$, said system comprising:
at least one trapping means to define an impurities trap having an inlet and an outlet, said at least one trapping means being adapted to trap at least one interfering impurity without affecting the at least one impurity to be measured;
means for reducing the effect of variations in moisture content within the gas sample on measurement of a first impurity to be measured, wherein said first impurity is an impurity other than $H_2O$, by adding moisture to the gas sample;
a plasma cell of a plasma emission system serially connected to said reducing means for generating an emission light representative of a concentration within the gas sample of at least said first impurity to be measured; and
processing means operatively connected to the emission cell for processing said emission light and providing the concentration of at least said first impurity to be measured.

18. The system according to claim 17, wherein said at least one trapping means comprises a molecular sieve for trapping $H_2O$ impurities, a reduced copper based catalyst for trapping oxygen impurities, a palladium based catalyst for trapping hydrogen impurities, a nickel based catalyst for trapping CO, $CO_2$ and non-methane hydrocarbon impurities, and an activated carbon based catalyst for trapping organic compounds.

19. The system according to claim 18, wherein said molecular sieve is provided with a pore diameter less than 4 Angstroms.

20. The system according to claim 18, wherein said activated carbon based catalyst comprises a deeply dehydrated coconut charcoal catalyst.

21. The system according to claim 17, further comprising temperature control means for maintaining a specific operating temperature of said at least one trapping means.

22. The system according to claim 17, wherein said reducing means is temperature controlled.

23. The system according to claim 17, wherein said reducing means comprises a permeation tube.

24. The system according to claim 23, wherein said permeation tube is temperature controlled.

25. The system according to claim 17, further comprising flow control means for keeping a flow of the gas sample constant throughout the impurities trap and the reducing means.

26. The system according to claim 17, further comprising an insulating enclosure mounted around said plasma cell for insulating said plasma cell from surroundings.

27. The system according to claim 17, wherein said gas sample comprises argon and said first impurity to be measured comprises nitrogen.

28. The system according to claim 17, wherein said processing means comprise collecting means for collecting said emission light at a specific emission wavelength not subjected to spectral interference to provide an emission signal representative of a concentration of the impurity to be measured, said processing means further comprising a microprocessor for processing said emission signal and providing said concentration of said impurity to be measured.

29. The system according to claim 28, further comprising adjusting means for adjusting a driving power of the plasma cell according to the concentration of the impurity to be measured.

30. The system according to claim 28, wherein said processing means is further provided with background collecting means for collecting a background emission light generated by said plasma cell at an emission wavelength neighbouring the specific emission wavelength to provide a background emission signal, said microprocessor being adapted for subtracting the background emission signal from the emission signal to provide a net emission signal representative of the net emission of the impurity to be measured, thereby cancelling background variations.

31. The system according to claim 28, wherein said processing means are provided with a correcting algorithm for compensating a non-linearity of the emission signal according to the concentration of the impurity to be measured.

32. The system according to claim 28, further comprising measuring means for measuring a plasma pressure of the plasma cell, said processing means being further adapted for compensating the emission signal according to the plasma pressure.

33. The system according to claim 17, further comprising a reference plasma cell connected in parallel with the emission cell for generating a reference emission light representative of a concentration of the impurity to be measured, said processing means being adapted to process said reference emission light for providing a level of the concentration of the impurity to be measured, said system further comprising adjusting means for adjusting a driving power of the plasma cell according to the level of the concentration of the impurity to be measured.

* * * * *